United States Patent
Dey et al.

(10) Patent No.: US 6,804,937 B2
(45) Date of Patent: Oct. 19, 2004

(54) PACKAGE WINDING MACHINE

(75) Inventors: Clifford A. Dey, Riegelsville, PA (US); Robert J. Cerwin, Pipersville, PA (US); Thomas J. Zingale, San Angelo, TX (US); Konstantin Ivanov, Basking Ridge, NJ (US); Delfin A. Lorenzo Iglesias, Guaynabo, PR (US); Manfred Hild, Schorndorf (DE); Manfred Reiser, Hertmannsweiler (DE); Bernard Wachter, Backnang (DE)

(73) Assignee: Ethicon, Inc., Somerville, NJ (US)

( * ) Notice: Subject to any disclaimer, the term of this patent is extended or adjusted under 35 U.S.C. 154(b) by 0 days.

(21) Appl. No.: 10/387,782

(22) Filed: Mar. 13, 2003

(65) Prior Publication Data

US 2004/0177594 A1 Sep. 16, 2004

(51) Int. Cl.[7] .............................................. B65B 63/04
(52) U.S. Cl. ........................... 53/430; 53/118; 206/63.3
(58) Field of Search ........................... 53/430, 116, 118; 206/63.3, 339

(56) References Cited

U.S. PATENT DOCUMENTS

| | | | | |
|---|---|---|---|---|
| 3,618,282 A | * | 11/1971 | Hagel et al. .................. 53/430 |
| 3,975,883 A | * | 8/1976 | Besnyo et al. ................ 53/430 |
| 5,271,495 A | * | 12/1993 | Alpern ...................... 206/63.3 |
| 5,438,746 A | * | 8/1995 | Demarest et al. .......... 29/564.6 |
| 5,473,810 A | * | 12/1995 | Demarest et al. .............. 53/118 |
| 5,473,854 A | * | 12/1995 | Demarest et al. .............. 53/116 |
| 5,487,216 A | * | 1/1996 | Demarest et al. .............. 53/118 |
| 5,491,954 A | * | 2/1996 | Sobel .......................... 53/116 |
| 5,660,024 A | * | 8/1997 | Ivanov et al. .................. 53/430 |
| 5,661,954 A | * | 9/1997 | Ivanov et al. .................. 53/430 |
| 5,664,404 A | * | 9/1997 | Ivanov et al. .................. 53/430 |
| 5,667,155 A | * | 9/1997 | Cerwin et al. ............ 242/472.5 |
| 5,695,138 A | * | 12/1997 | Daniele et al. ............. 242/520 |
| 5,788,062 A | * | 8/1998 | Cerwin et al. ............. 206/63.3 |
| 5,868,244 A | * | 2/1999 | Ivanov et al. .............. 206/63.3 |
| 5,873,212 A | * | 2/1999 | Esteves et al. ................ 53/118 |
| 5,920,482 A | * | 7/1999 | Demarest et al. ........... 700/159 |
| 5,956,927 A | * | 9/1999 | Daniele et al. ............... 53/430 |
| 5,964,075 A | * | 10/1999 | Daniele et al. ............... 53/118 |
| 5,970,686 A | * | 10/1999 | Demarest et al. ............. 53/430 |
| 5,983,601 A | * | 11/1999 | Blanch et al. ................ 53/430 |
| 5,987,848 A | * | 11/1999 | Blanch et al. ................ 53/118 |
| 6,014,851 A | * | 1/2000 | Daniele et al. ............... 53/430 |
| 6,032,343 A | * | 3/2000 | Blanch et al. ................ 53/118 |
| 6,047,815 A | * | 4/2000 | Cerwin et al. ............. 206/63.3 |
| 6,076,255 A | * | 6/2000 | Shikakubo et al. ........... 29/715 |
| 6,081,981 A | * | 7/2000 | Demarest et al. ........ 29/407.08 |
| 6,098,796 A | * | 8/2000 | Januzeli et al. ............ 206/63.3 |
| 6,105,339 A | * | 8/2000 | Pohle et al. .................. 53/415 |
| 6,135,272 A | * | 10/2000 | Sobel et al. ................ 206/63.3 |
| 6,138,053 A | * | 10/2000 | Demarest et al. ........... 700/117 |
| 6,205,748 B1 | * | 3/2001 | Daniele et al. ............... 53/430 |
| 6,463,719 B2 | * | 10/2002 | Dey et al. ..................... 53/430 |

* cited by examiner

Primary Examiner—Stephen F. Gerrity
(74) Attorney, Agent, or Firm—Emil Richard Skula

(57) ABSTRACT

A machine and process for packaging armed sutures into tray packages. The machine has a frame with a rotatable indexing disc member mounted to the top of the frame. A plurality of tool nests are rotatably mounted to the top of the indexing disc. Tray packages mounted in the toll nests are rotated to wind sutures into a suture channel in the packages. A stylus having a front nose member and a rear heel member guides suture into the suture channel. Channel winding pins in the winding tooling provide for an arranged wind of suture in a suture channel of the tray packages. The machine has an in-line printer and a punching machine for printing and punching paper covers from strips of stock material, which are then mounted to the tray packages.

11 Claims, 25 Drawing Sheets

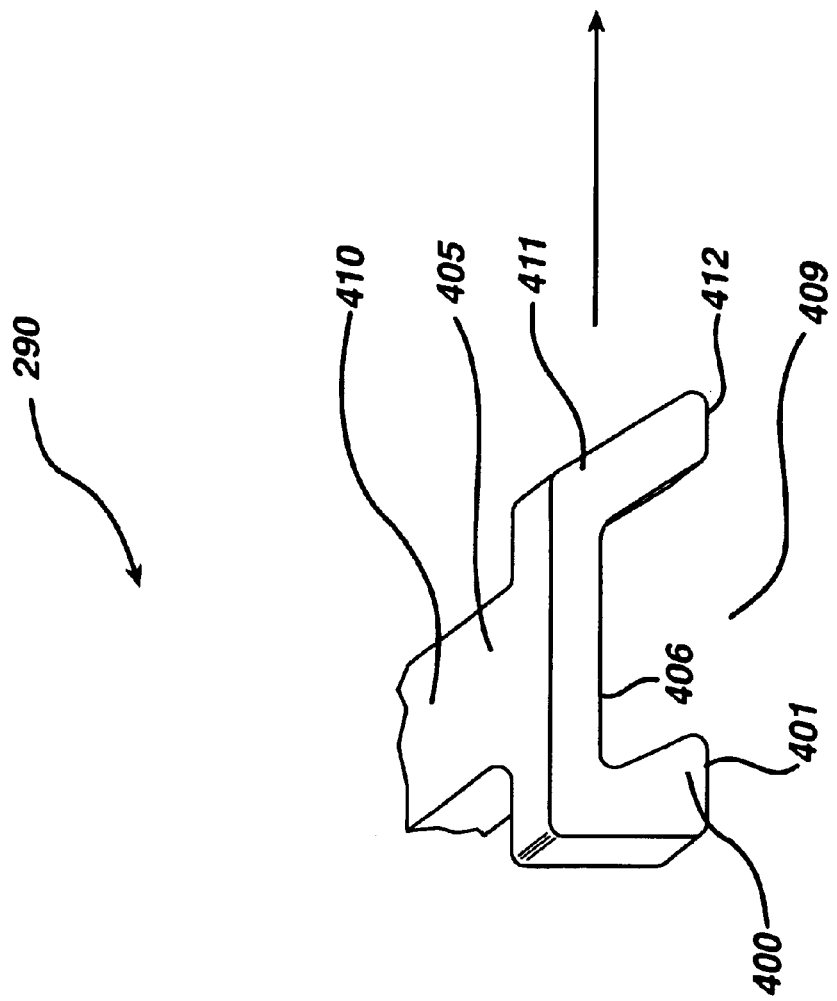
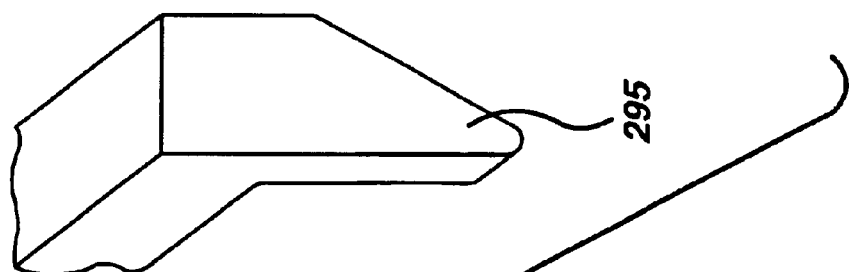
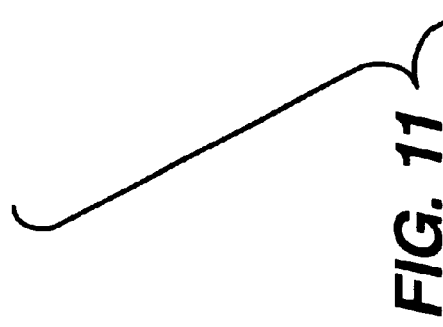

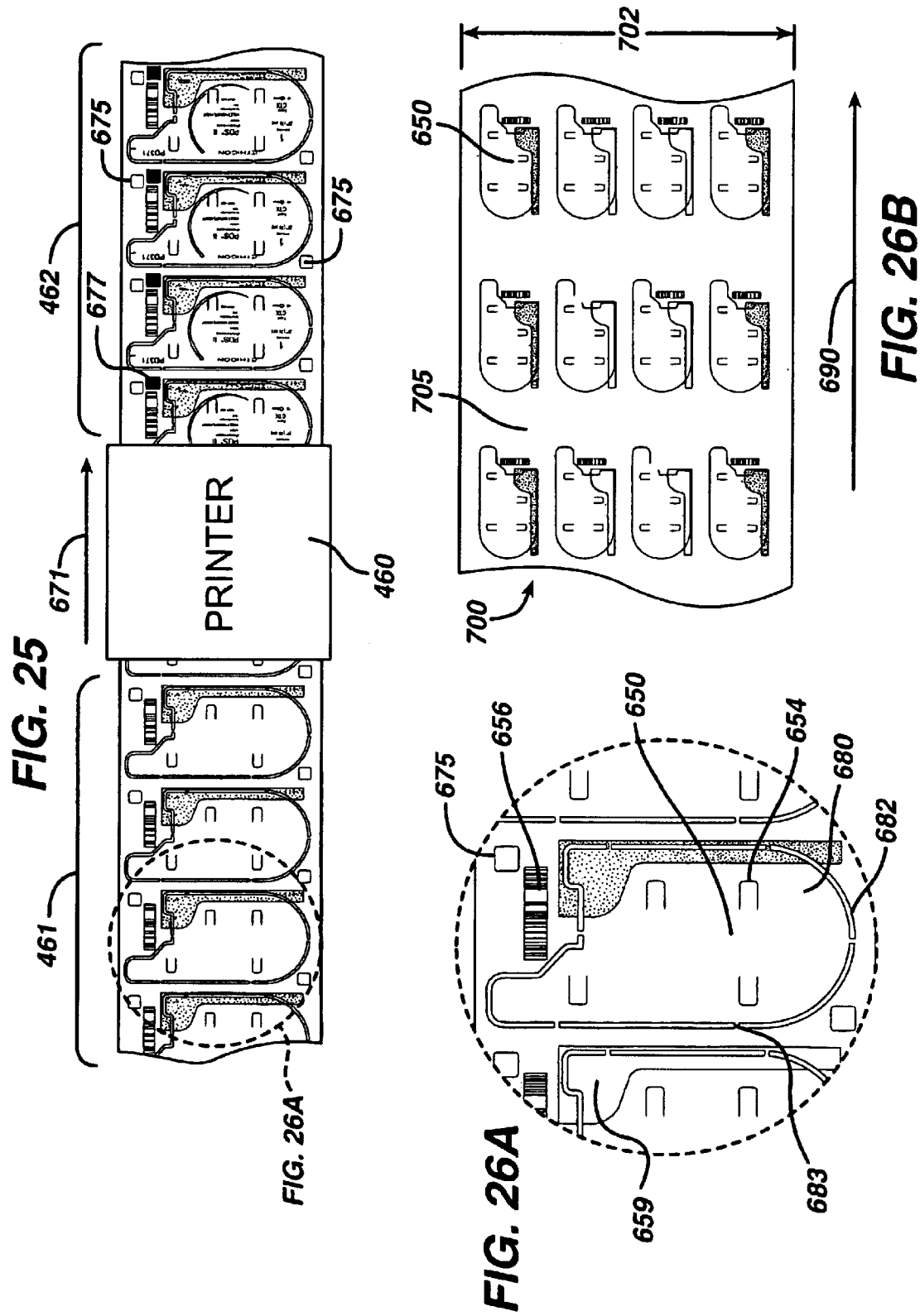

PACKAGE WINDING MACHINE

TECHNICAL FIELD

The field of art to which this invention relates is packaging machinery, more specifically, packaging machinery for packaging surgical needles and sutures, and methods of packaging surgical needles and sutures.

BACKGROUND OF THE INVENTION

Surgical sutures having surgical needles attached to one or both ends are well known in the medical arts. Sutures having a single needle attached to one end are known as single-armed sutures, while sutures having needles attached to both ends are known as double-armed sutures. Sutures not having surgical needles mounted to either end are referred to as unarmed sutures. Double-armed sutures find particular utility in the following types of surgical procedures: cardiac valve replacement surgery, cardiac surgery, and bowel surgery.

In the past, surgical sutures were hand packaged into specially designed suture packages. Typically, the sutures were wound using conventional winding fixtures having winding pins. Although there may have been advantages associated with the hand winding methods of the prior art, one major disadvantage was that they were unnecessarily time consuming. In order to maintain high quality and to reduce costs, manufacturers of surgical sutures and surgical needles have developed high-speed packaging processes for packaging surgical needles and sutures into specially designed packages. Packages for surgical needles and sutures are well know in the art The packages range from simple folder packages to more complex, molded tray packages suitable for automated, high speed winding and packaging processes. A typical tray package has a winding channel in which the suture is contained. Various moveable doors or hinged members are used to cover the winding channel to maintain the wound suture in place. The tray packages typically have a needle park to retain surgical needles that are mounted to one or both ends of the surgical needles. The sutures are wound into the winding channels by mounting the trays in a rotatable nest member, and rotating the nest and tray while using a stylus member to direct and locate the suture in the channel in a wound pattern. Examples of packages which can be used in high speed winding applications are contained in U.S. Pat. Nos. 5,213,210, 5,236,083, 5,284,240, 6,098,796, and 6,135,272, the disclosures of which are incorporated by reference. High speed winding machines for packaging surgical sutures in such surgical suture packages are disclosed for example in U.S. Pat. Nos. 5,664,404 and 6,032,343 which are incorporated by reference.

Although the packaging machines and processes of the prior art are adequate for their intended use, there are certain types of surgical sutures which are particularly difficult to adapt to high speed winding or packaging machine operations. For example, suture for use in cardiac and cardiovascular surgical procedures is very delicate and any damage caused to the suture by handling or packaging can compromise the integrity of the sutures. In addition, it has been difficult to package such sutures in packages using high-speed automatic packaging machinery due in part to the fine gauge of the sutures. Also, it previously has not been possible to package double armed sutures in tray packages using high-speed winding equipment.

Accordingly, there is a need in this art for novel high-speed packaging machinery and processes for packaging surgical needles and sutures. There is a constant need in this are for novel winding apparatuses and methods to provide for high packaging throughputs, while maintaining the quality and integrity of the surgical sutures and the packages.

SUMMARY OF THE INVENTION

It is an object of the present invention to provide novel packaging machines and methods to efficiently and effectively load surgical sutures into a tray package having a suture winding channel in such a way that the sutures are not damaged during the loading process, and such that the sutures dispense easily in the field without damage to the suture.

It is further object of the present invention to provide a machine and a process for electronically printing and affixing a cover to a tray package having a suture winding channel with a surgical suture wound in the channel, and then optionally loading the packages with the labels into magazines that are suitable for automatic processing in downstream operations.

Accordingly, an apparatus or machine for winding surgical sutures into tray packages is disclosed. The apparatus has a machine frame having a top, a bottom, sides and an interior. A disc member is rotatably mounted to the top of the frame, the disc member has a periphery, top, a bottom and a side about the periphery of the disc member. There are a plurality of tool nests. Each tool nest is rotatably mounted to the top of the disc member. Each such tool nest has a nest frame, having a top, a bottom and sides. At least two winding pin members extending up from the top of the nest frame. A rotatable tool is mounted to the machine frame, said tool being displaceable downwardly to engage with the pin members on the nest frame, such that rotation of the tool will rotate the tool nest, wherein said rotatable tool has a top and a bottom. A plurality of channel winding pin members extend down from the bottom of the rotatable tool. There is a cam track member that extends down from the bottom of the rotatable tool. The cam track member has a pair of opposed longitudinal sides and a pair of opposed curved ends connecting the longitudinal sides. The cam track member has a first width along the longitudinal sides and a second width along the curved ends, wherein the first width is greater than the second width. A stylus member is movably mounted to the machine frame, for cooperation with the tool nests. The stylus member has a stylus frame having a top, sides and a bottom. A stylus is mounted to the bottom of the stylus frame having a front nose member and a rear heel member separated by a suture opening. The stylus has a top surface and a bottom surface. A door dosing member extends down from the bottom of the stylus frame adjacent to the stylus. The stylus member operatively engages the cam track member. Optionally, the packaging machine has an in-line printer associated therewith for printing package covers, and, a punching apparatus for punching printed covers from a printed strip of cover material.

Yet another aspect of the present invention is the combination of a suture tray package and a packaging machine. The packaging machine has a machine frame having a top, a bottom, sides and an interior. A disc member is rotatably mounted to the top of the frame. The disc member has a periphery, top, a bottom and a side about the periphery of the disc member. There are a plurality of tool nests, each tool nest is rotatably mounted to the top of the disc member. Each tool nest has a nest frame, having a top, a bottom and sides. At least two winding pin members extend up from the top of the nest frame. A rotatable tool is mounted to the machine frame. The rotatable tool is capable of being displaced downwardly to engage with the pin members on the nest frame, such that rotation of the tool will rotate the tool nest The rotatable tool has a top and a bottom. A plurality of channel winding pin members extend down from the bottom of the rotatable tool. There is a cam track member that extends down from the bottom of the rotatable tool. The cam track member has a pair of opposed longitudinal sides and a pair of opposed curved ends connecting the longitudinal sides. The cam track member has a first width along the longitudinal sides and a second width along the curved ends, wherein the first width is greater than the second width. A stylus member is movably mounted to the machine frame, for cooperation with the tool nests. The stylus member has a stylus frame having a top, sides and a bottom. A stylus is mounted to the bottom of the stylus frame. The stylus has a front nose member and a rear heel member separated by a suture opening. The stylus has a top surface. A door closing member extends down from the bottom of the stylus frame adjacent to the stylus. The stylus operatively engages the cam track member. The suture tray package has a top and a bottom. The tray package has a flat base member having a top and an outer periphery. An outer wall extends up from the base member about the periphery of the base member. An inner wall, interior to the outer wall, extends up from the top of the base member, said inner wall has a top, and the inner wall is spaced away from the outer wall to form a suture channel. A plurality of door members extends out from the top of the inner wall over the winding channel, each such door member has a proximal end and a distal end, and opposed sides. There are a plurality of openings between at least some of the door members for receiving channel winding pin members. At least two needle park members extend up from the top of the base member. The needle park members are located interior to the inner wall. The tray package is mounted in a tool nest. The packaging machine of the combination can optionally have an in-line printer associated therewith for printing package covers, and, a punching apparatus for punching printed covers from a printed strip of cover material.

The tray package of the combination can optionally have a cover for mounting to the top of the package.

Still yet another aspect of the present invention is a method of loading and winding a surgical needle and suture assembly into a tray package having a suture channel using the packaging machines of the present invention.

These and other aspects and features and advantages of the present invention will become more apparent from the following description and accompanying drawings.

BRIEF DESCRIPTION OF THE DRAWINGS

FIG. 11 is a perspective view illustrating a winding stylus assembly used with the packaging machines of the present invention to guide suture into a channel of a tray package.

FIG. 25 is a plan view of a paper strip used to manufacture the covers of FIGS. 23 and 24, before and after printing.

FIG. 26A is a partial, magnified plan view of the paper cover strip of FIG. 25 illustrating the die cutting thereon.

FIG. 26B is a plan view of a paper cover strip typically produced by a conventional layout for a rotary converting press.

DETAILED DESCRIPTION OF THE INVENTION

The machines and processes of the present invention are preferably useful to package conventional surgical sutures and needles into tray packages having winding packages. The sutures may be armed, that is, having a conventional surgical needle mounted to one or both ends, or may be un-armed without a surgical needle on either end.

Figure 1:
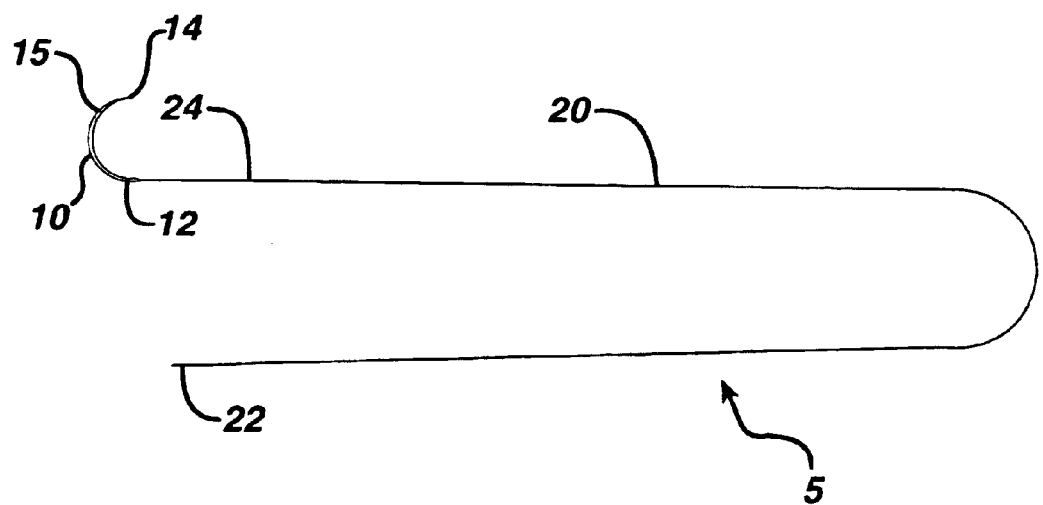
FIG. 1 is a plan view of a surgical suture having a surgical needle mounted to one end thereof.

Surgical sutures and packages assembled by the machines and processes s of the present invention are described herein are illustrated in FIGS. 1–5. Referring first to FIG. 1, an armed surgical suture with attached needle assembly 5 is illustrated. The assembly 5 is seen to have surgical suture 20 having distal end 24 and proximal end 22. Assembly 5 is also seen to have surgical needle 10 having pointed distal end 14 and proximal suture mounting end 12, as well as midpoint 19 and needle body 15. The distal end 24 of suture 20 is seen to be mounted to the proximal end 12 of surgical needle 10.

Figure 2:
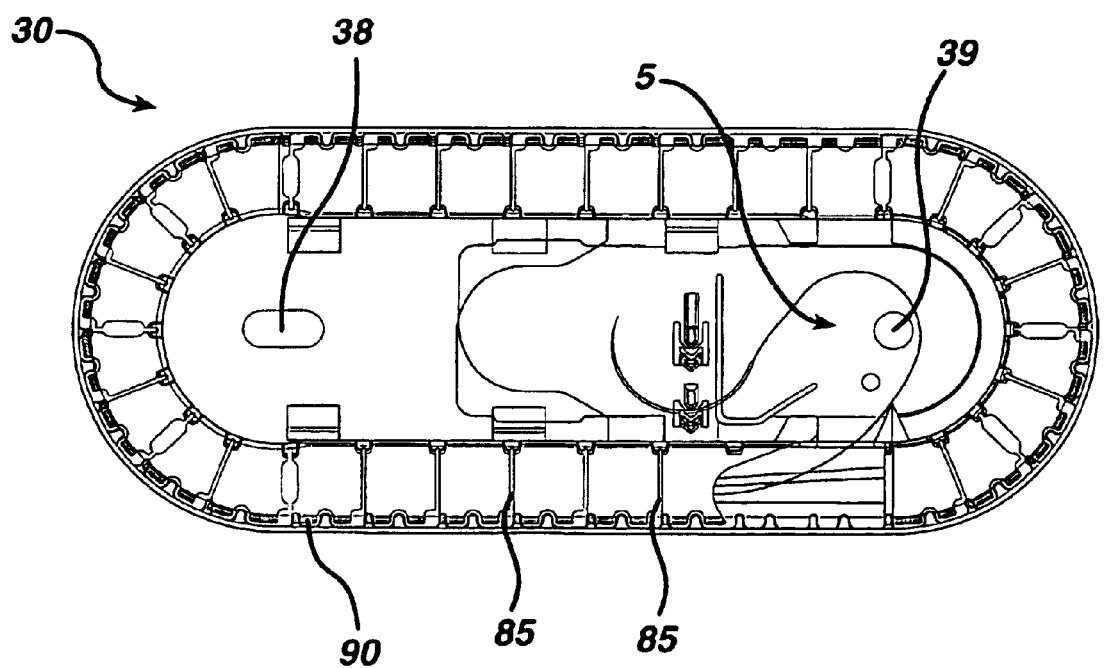
FIG. 2 is a plan view of a tray package having a suture winding channel and a needle park, with the needle and suture of FIG. 1 contained therein.
Figure 3:
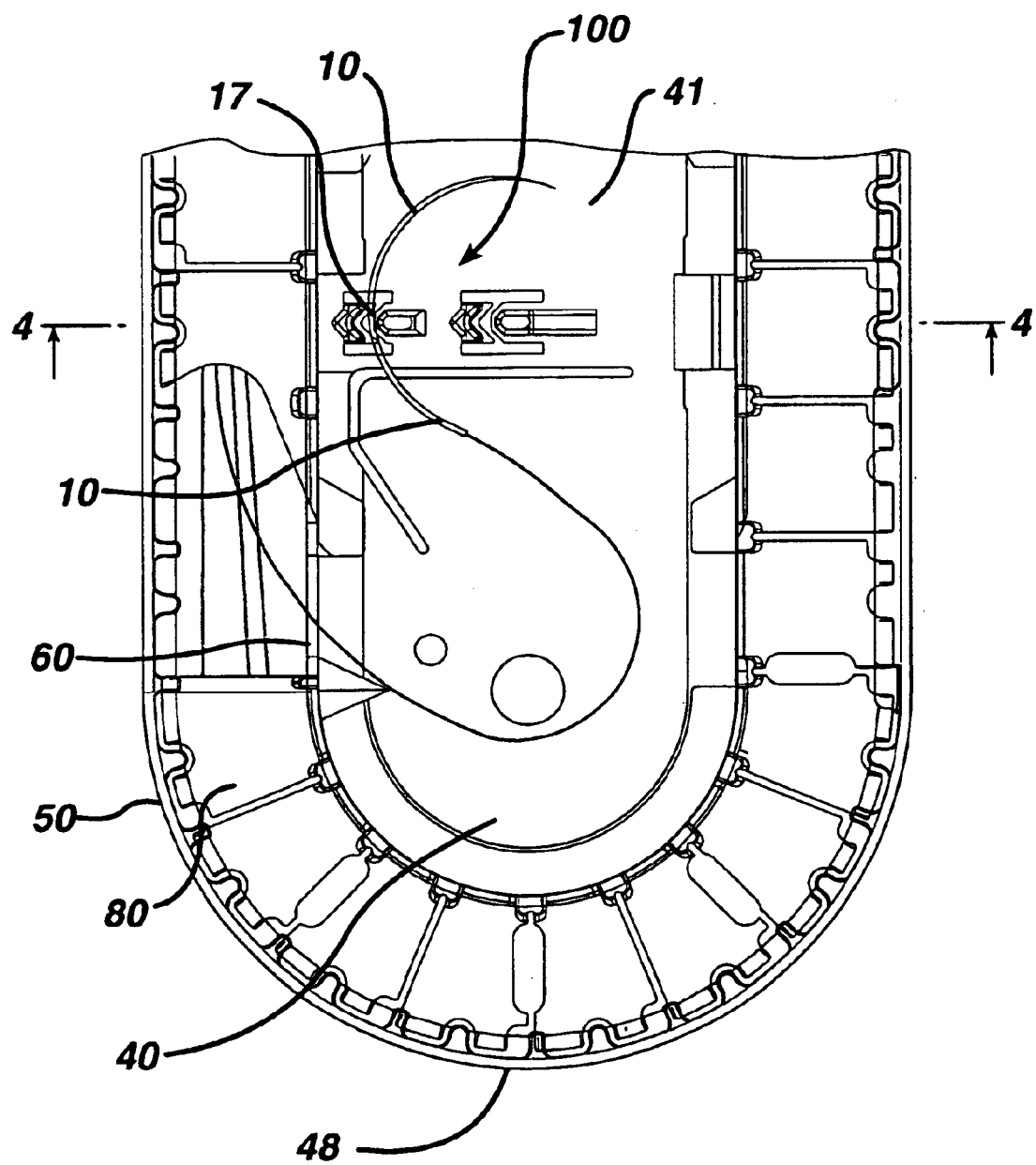
FIG. 3 is a magnified partial view of the package of FIG. 2 illustrating the needle mounted in the needle park.

A molded package tray 30 having a winding channel to contain the suture assembly is seen in FIG. 2. Referring also to FIG. 3, the package tray 30 is seen to have a planar base 40, parallel sides with essentially semicircular ends 48, and having top 41 and bottom 42. An outer wall 50 extends up from base 40 about the outer periphery of base 40. Spaced inward from outer wall 50 and substantially parallel thereto is inner wall 60 that extends up from top 41 of base 40. Outer wall 50, inner wall 60, and a section of top 41 A partially define a suture winding channel 70 having bottom 72. A plurality of flexible flap members 80 are seen extending generally radially outward and sloping downward from the top 62 of inner wall 60 over and into winding channel 70. Referring to the cross-sectional view of FIG. 4, the flaps 80 extend to a distal end 82 that contacts the outer wall 50 where it meets with a radiused profile inner surface 74 of bottom 72. The top surface 41 of package base 40, the inner surface of outer wall 50, the outer surface of inner wall 60, and the flap members 80 completely define the winding channel 70 which confines suture strands 28 of suture 20.

Figure 4:
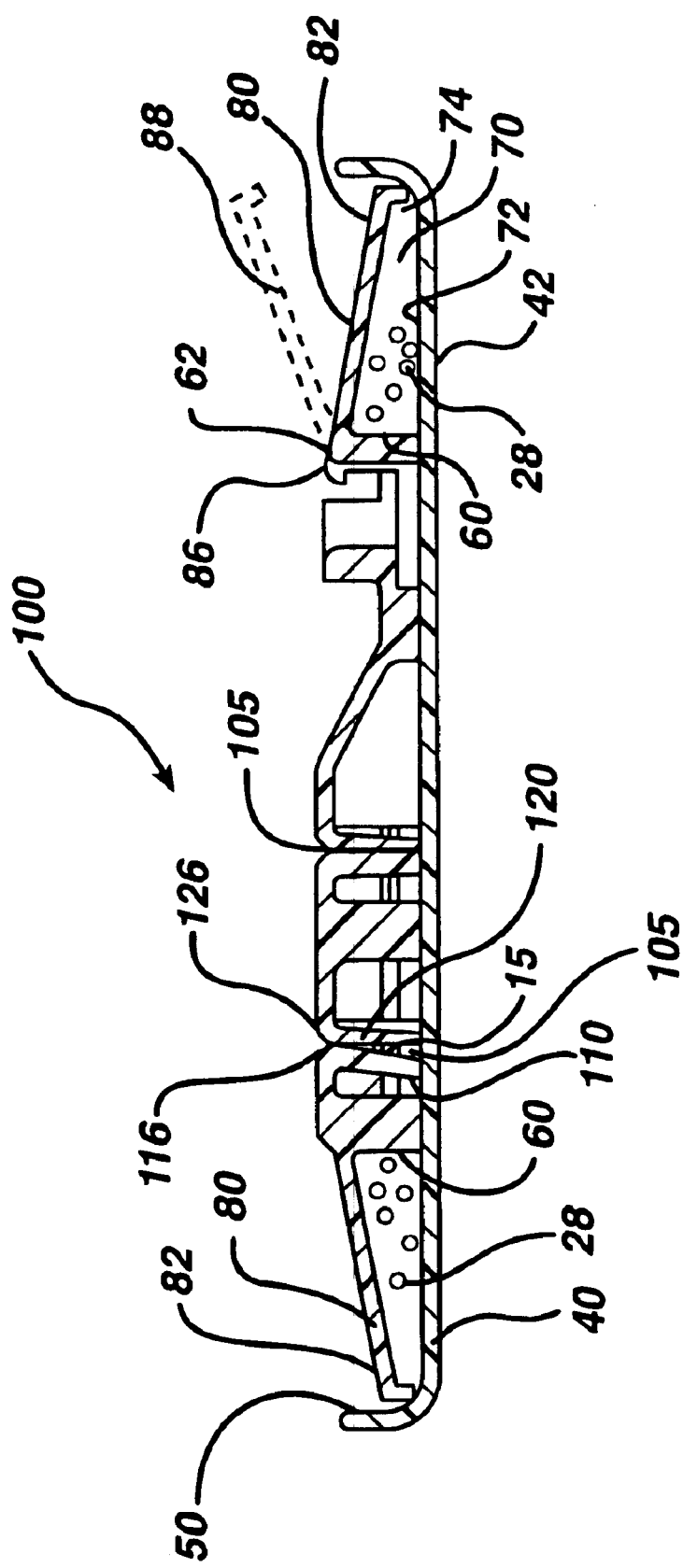
FIG. 4 is a cross-sectional view taken along View Line 4—4 of the package of FIG. 2.

The package tray 30 is made of resilient material such as plastic, thereby affording properties to the flap members 80 that allow them to be mechanically hinged, about their connection areas or hinges 86, upwardly to position 88 shown in dashed line illustration, and when released, spring back to essentially their resting downward sloping position. Molded slots 85 are seen to separate the individual flaps 80, allowing them to be individually flexed open as illustrated in FIG. 4, with adjacent flaps 80 remaining closed. Sequentially opening and closing the flaps 80 allows the suture 20 to be wound into the winding channel 70 by the machines and methods of the present invention.

Located in the lower central portion of the package tray 30 is the needle holding structure 100, referred to herein and conventionally in the art as a "needle park". Needle park 100 is seen in FIGS. 3 and 4. Needle park 100 is seen to have cantilevered members 110 and stationary members 120 separated by gap 105. The loading of a needle 10 into the needle park 100 is done by pressing the needle body 15 in a direction perpendicular to the tray base 40 at roughly the mid-point 17 of the needle, against upper chamfered sections 116 and 126 of members 110 and 120, respectively, causing the cantilevered member 110 to flex away from the stationary member 120 while maintaining a spring force or bias against the needle body 15, thereby securing by a frictional force the needle 10 in needle park 100 against dislodging due to subsequent exposure to package handling or shipping vibration.

Figure 5:
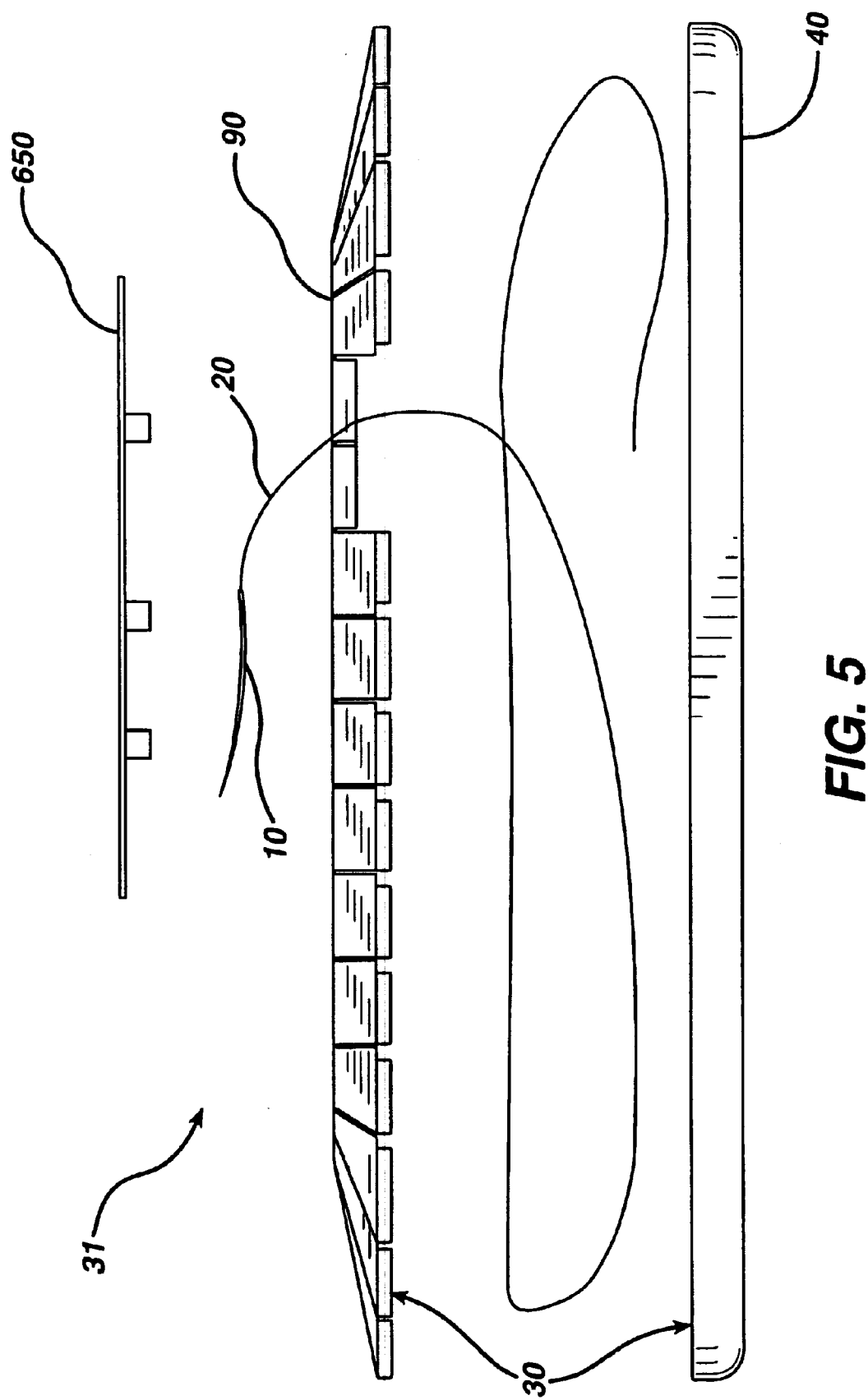
FIG. 5 is an exploded side view of the package and suture of FIG. 2.

Preferably, the package 10 is itself assembled from multiple components to form an assembled tray package that can be loaded with a surgical suture assembly 5. As seen in FIG. 5, the components include the previously described base member 40 to which is mounted a cover member 90. These components are assembled and fastened in combination with an upstream molding process, said assembly operations are not relevant to the package machine described herein, to make the package tray 30. A paper cover 650 is printed and affixed to the top of the package tray 30, after suture assembly 5 is loaded. Also illustrated in FIG. 5 is the coiled suture 20 and the needle 10.

Figure 6:
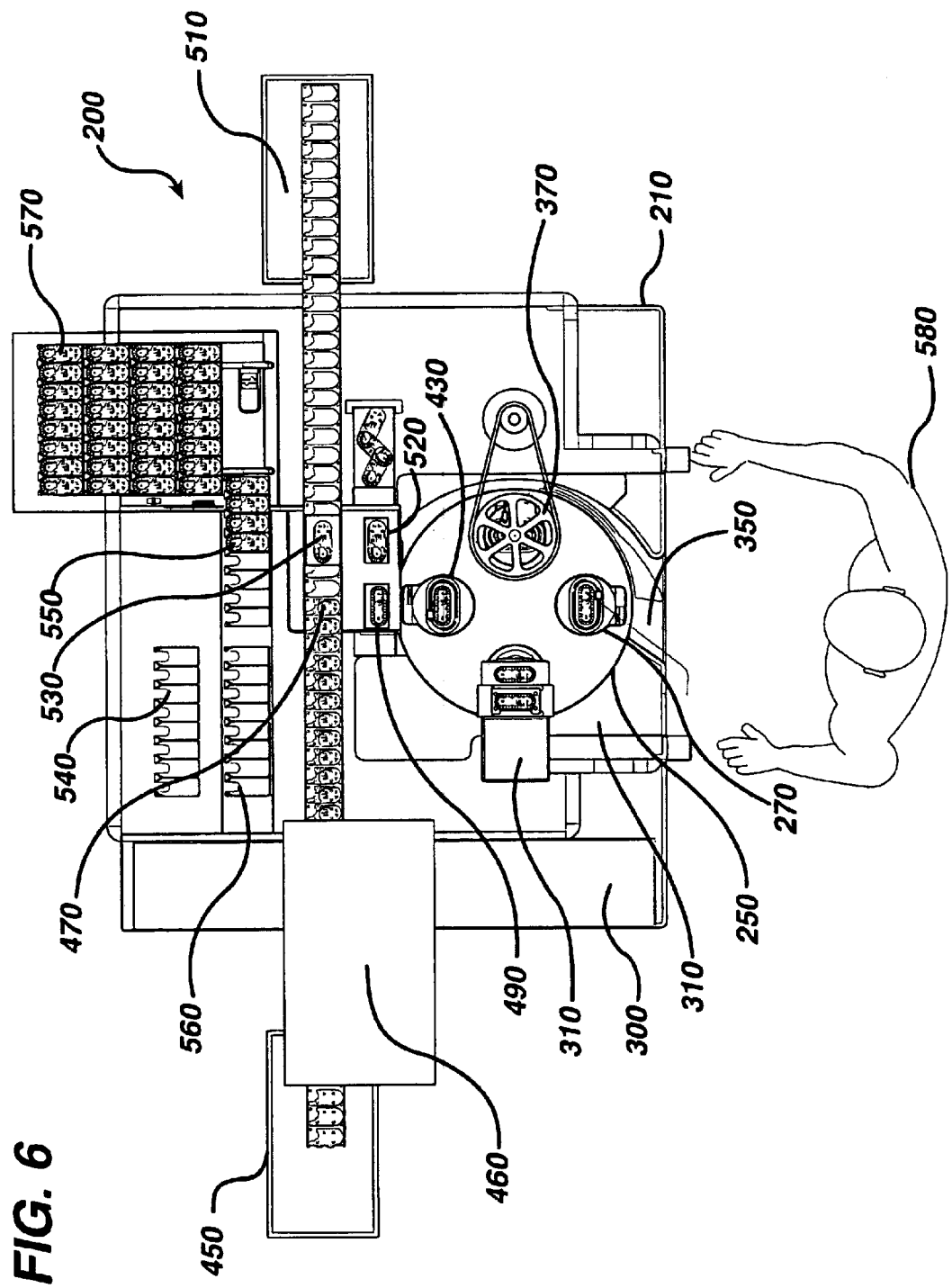
FIG. 6 is a plan view of a packaging machine of the present invention.

A particularly preferred embodiment of a packaging machine of the present invention is seen in FIG. 6. The zipper package assembly machine 200 is a rotary index type combined with linear motions to transport the package through its assembly sequence. The machine 200 is seen to include a machine frame and enclosure 210, a main rotary indexing disc shaped turret 250, an equally spaced plurality of tool nests 270 rotatingly mounted thereon, an electronic controls enclosure 300, a machine top tool plate 310 with feeding and assembly stations positioned and fixedly mounted thereto.

The operating functions on the machine 200 described in more detail hereinbelow are the molded tray hopper and feeding station 330, suture load station 350, winding station 370, transfer station 430, paper lid strip feed container 450, paper lid printer 460, lid punch and feed station 470, lid assembly station 490, paper lid scrap bin 510, accept/reject station 520, demagnetization station 530, magazine hopper 540, magazine load station 550, empty magazine feed station 560, and completed product magazine discharge station 570. The feeding of suture assemblies 5 to the machine can be done manually, as illustrated for example by operator 580, or automatically by robot or other device (not shown).

Figure 7:
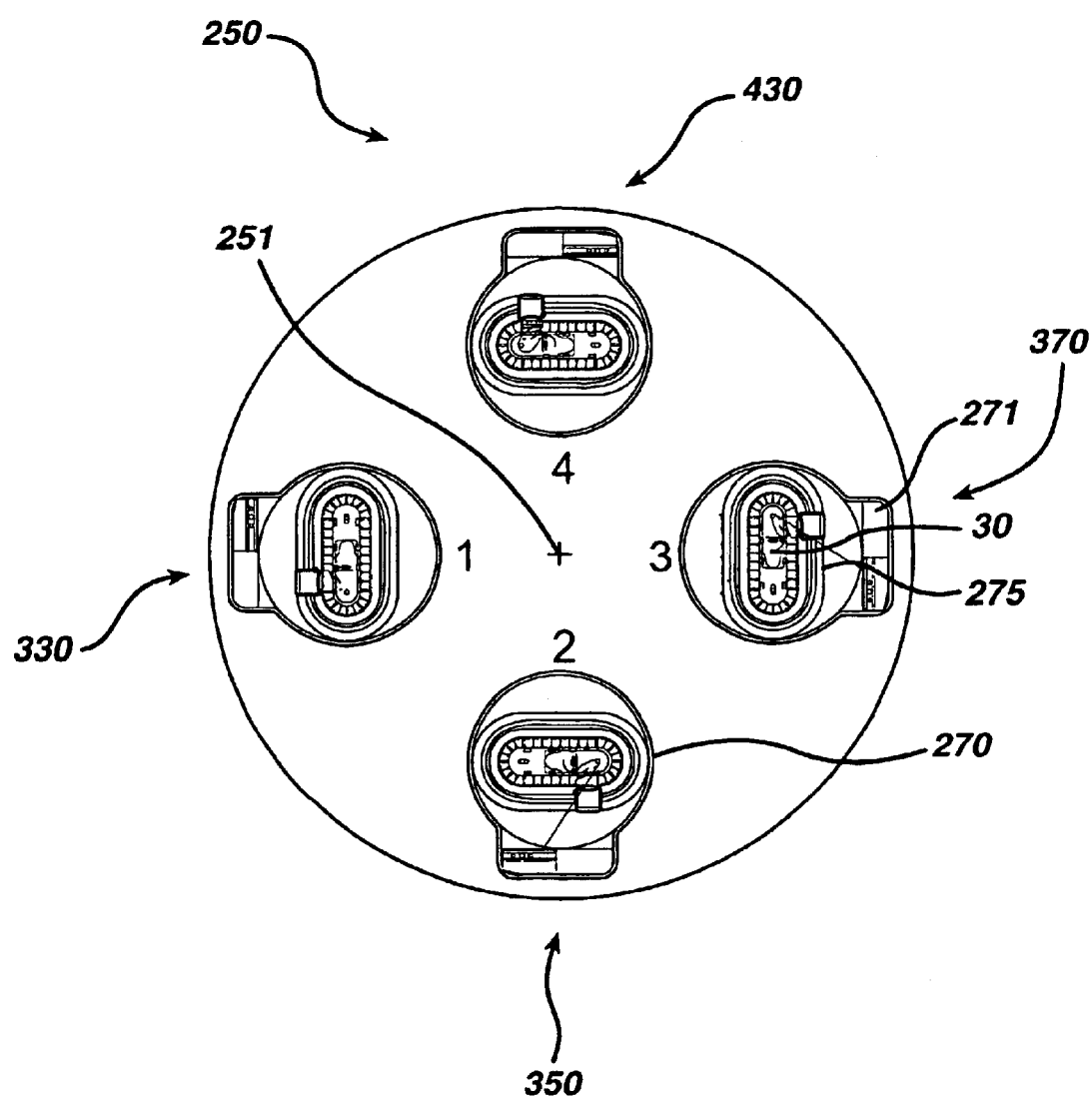
FIG. 7 is a plan view of illustrating the machine indexing turret and a plurality of tool nests thereon, of the packaging machine of FIG. 6

Referring now to FIG. 7, the indexing turret 250 and a plurality of identical tool nests 270 equally spaced around the periphery thereon are seen. The turret 250 is mounted rotatingly to frame 210 about a vertical turret axis 251. The turret 250, comprising four tool nests 270 in the preferred embodiment, moves in an index rotation 90° counterclockwise at each machine cycle.

Figure 8:
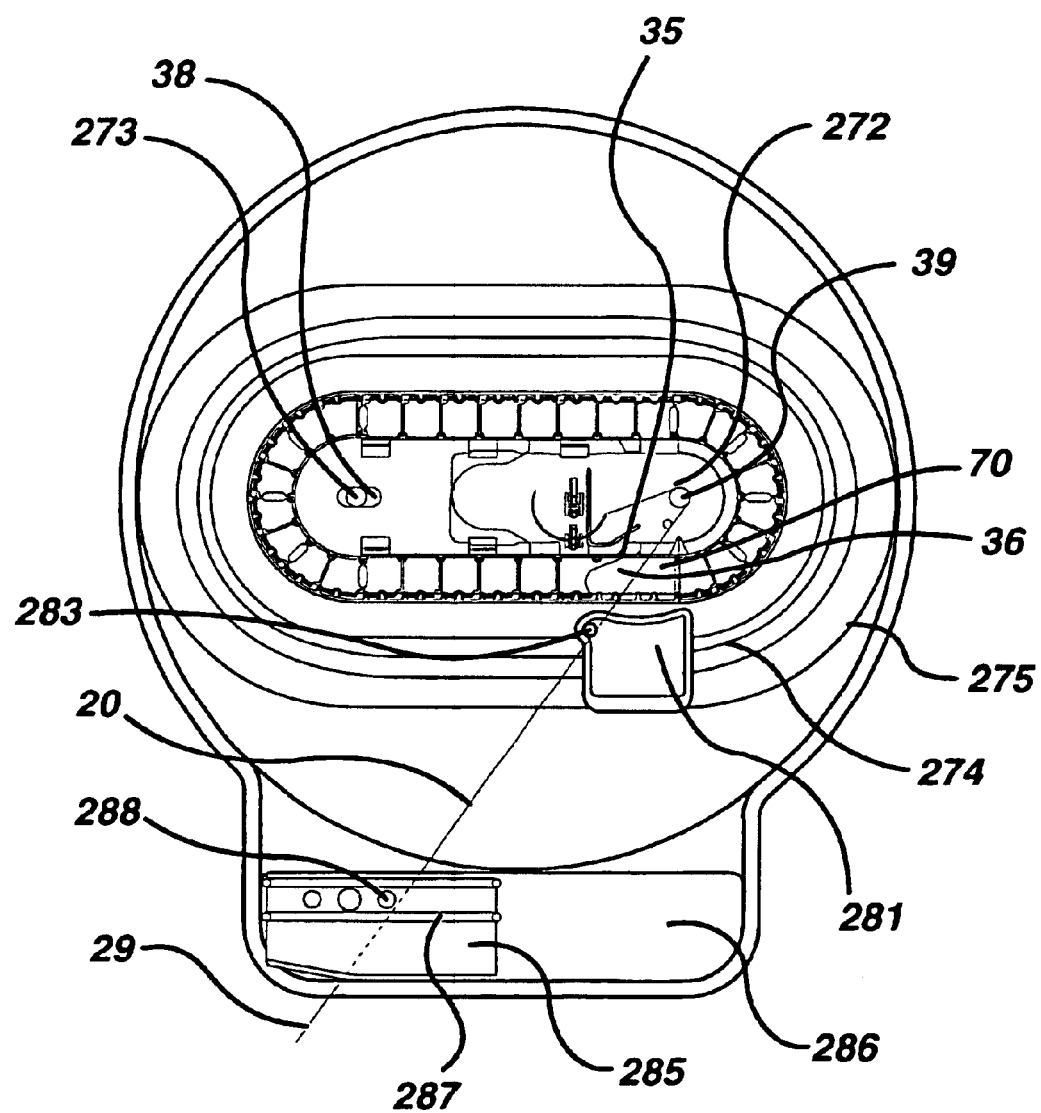
FIG. 8 is an enlarged plan view of a tool nest of FIG. 7.
Figure 9:
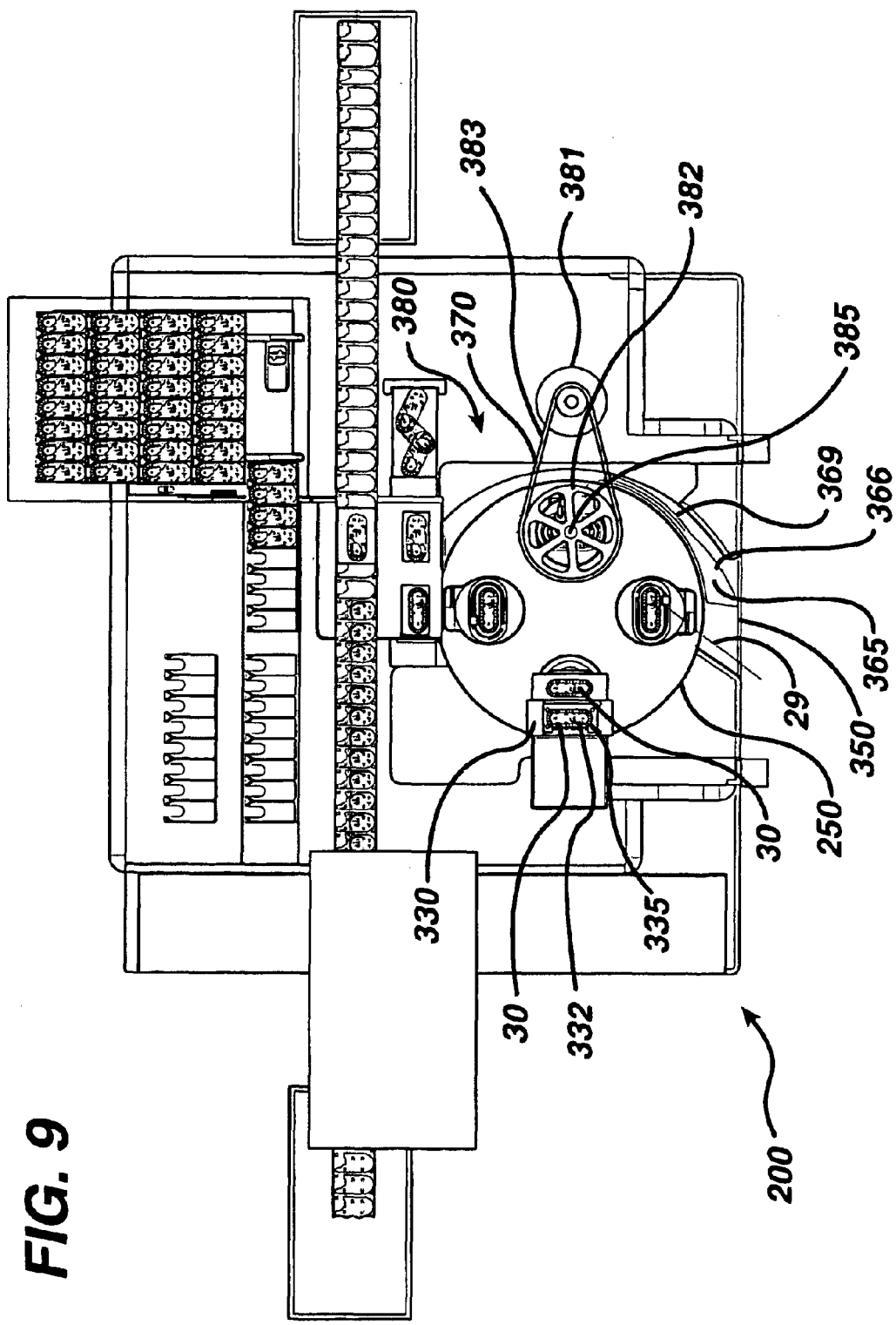
FIG. 9 is a magnified view illustrating the machine top the packaging machine of FIG. 6.

An enlarged plan view of the machine. 200 of FIG. 6 is seen in FIG. 9. The first station 330 loads an empty molded tray package 30 from a vertical stacking hopper 332 with a shuttle slide (not shown). The vertical stack of moldings 30 is contained by a plurality of fixed vertical rods that confine the moldings 30 by guiding on their outer edges, allowing the packages 30 to descend by gravity, being singulated and translated horizontally from the bottom of the stack by a typical slice type shuttle (not shown) as the machine is cycled. The shuttle gripper (not shown) places the empty molded tray 30 over winding pins 272 and 273 (See FIG. 8), so that corresponding slot 38 and hole 39 respectively in the tray 30 are coincident therewith.

The needle and suture assembly 5 are loaded into package 30 at station 350 as seen in FIG. 7, either manually or automatically. An enlarged view of the tooling nest 270 of FIG. 7 is seen in FIG. 8, illustrating a package tray 30 indexed into position from station 330 and after the needle and suture assembly 5 been inserted therein at station 350. As illustrated, the needle 10 is been pressed vertically downward into in the needle park 100, and the suture 20 is guided around the winding pin 272, over the winding stylus base 281 of winding stylus 290, against the stylus base pin 283, and under the friction hold down 285. Hold down weight block 285 exerts a gravitational force against a corresponding platform top surface 286 through resilient elastic bands 287 stretched therearound, thereby frictionally fixing the position of suture strands 20 therebetween. Elastic bands 287 are manufactured of soft, rubber-like material, to prevent damage to the suture strands 20. The winding pin 272, the stylus base pin 283, and the hold down vertical shaft 288, are positioned to locate the suture strand 20 through the gap 35 in the tray inner wall and generally within the stylus access opening 36 in the tray suture channel. The trailing end or loop 29 of the suture 20 beyond the hold down 285 hangs freely or is controlled by other means not part of the machine.

Referring to FIG. 9, the winding operation commences after the turret 250 indexes 90° counter clockwise, thereby moving the tool nest 270 and package 30 with needle and suture assembly 5 loaded at suture loading station 350 to suture winding station 370. The free suture trailing end 29 is pulled along by the 90° counter-clockwise index rotation of the turret 250 to a position 369 in proximity of the winding turret position 370, guided by a fixedly mounted trough 365 that is fabricated with a smooth surface 366 to prevent suture damage.

The details of the turret 250 are illustrated in FIG. 7. Each of the four tooling nests 270 are rotatable about their individual vertical axes, for example axis 271 for nest 270 at suture winding station 370, after a rotational latch within the turret mechanism (not shown) is disengaged. Referring to FIG. B, winding stylus base 281 is free to slide parallel to the suture channel 70 of the package tray 30, guided by cam tracks 274 in the tooling base 275 after being similarly mechanically disengaged.

Figure 10:
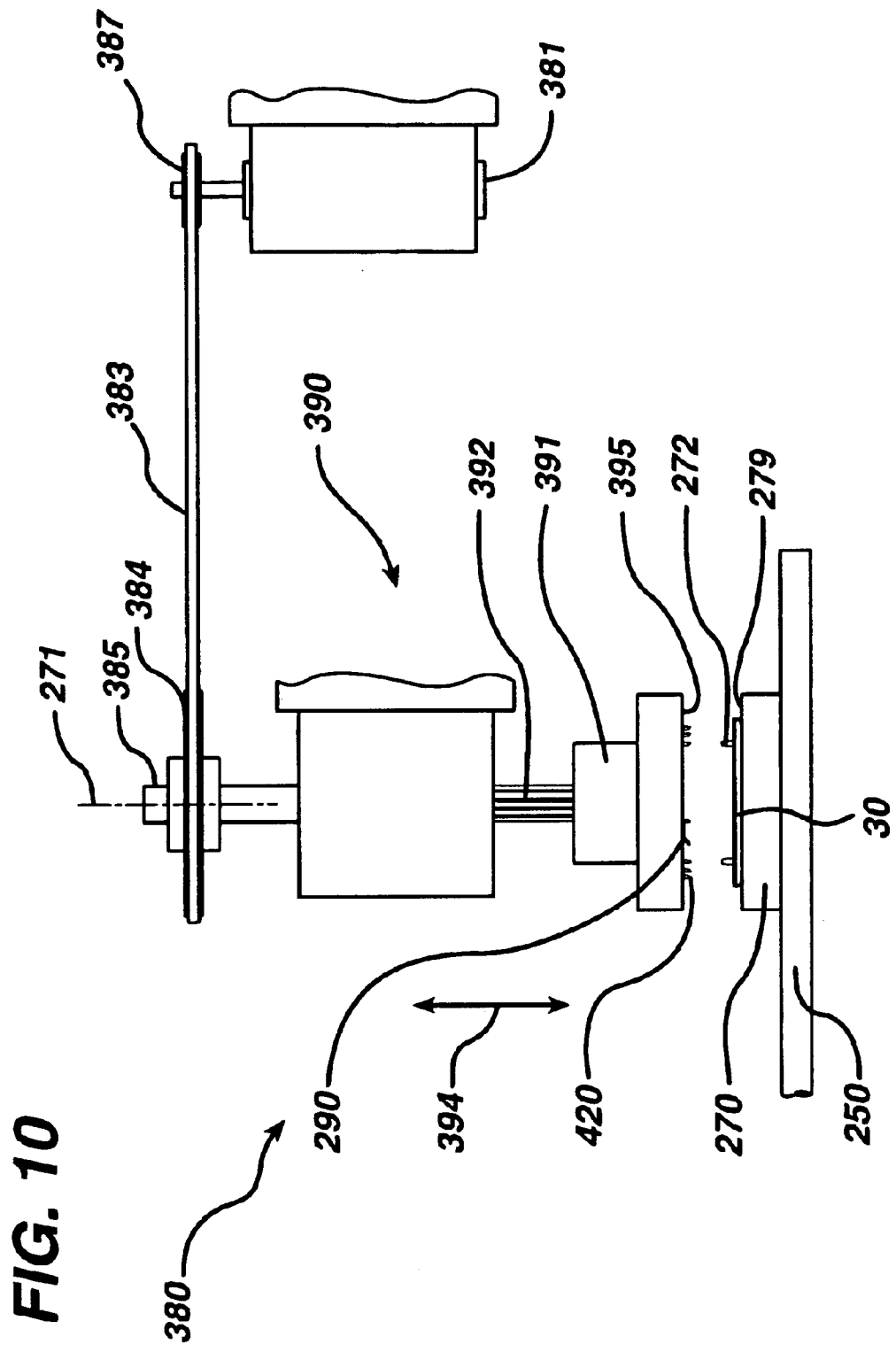
FIG. 10 is a schematic side view of a winding station used in the packaging machines of the present invention, illustrating the major elements thereof.

FIG. 9 and elevation view FIG. 10 illustrate the winding station power drive assembly 380, comprised of a servo motor 381, drive sprocket 382, toothed drive belt 383, and driven sprocket 384. A vertical shaft 385 is located by appropriate bearings (not shown), fixedly mounted to the machine frame and coaxial with the rotation axis 271 of the tool nest 270 therebelow.

Referring now to FIG. 10, turret 250 is shown after indexing tool nest 270, and the tray package tray 30 thereon, with a needle and suture assembly 5, not shown, assembled thereto, into a position under the winding tooling 390. The upper tooling assembly 391 fixed to the vertical shaft 385, vertically slideable on splines 392 thereon, in the direction of arrow 394, is vertically displaced downward and engaged with the lower tooling 270 therebelow. The lower surface 397 of the upper tooling 391 approaches the upper surface 279 of the lower tooling 270, essentially damping the package tray 30 therebetween. This downward vertical displacement also causes pins 272 and 273 in the lower tooling to engage mating holes (not shown) in the upper tooling 391, thereby causing the driven rotation of the upper tooling 391 by the belt 383 and sprocket 384 to likewise drive rotation of the lower tooling nest 270, now torsionally integral therewith, about vertical 271.

The winding stylus 290, described hereinbelow, is similarly engaged with the stylus base 281 (See FIG. 8), by meshing pins and mating holes therein (not shown). The suture held down 285 (See FIG. 8) is mechanically raised, minimally to prevent suture twisting, to remove frictional drag forces on the suture 20 during the winding operation.

The winding stylus assembly 290, as seen and illustrated in FIG. 11, comprises an insertion tool 410, a flap closing tool 295, and a mounting block 405. The stylus insertion tool 410 has a sloping nose member 411 and a heel member 400 extending down from opposite ends of support member 406, wherein the members 411 and 400 are separated by gap 409.

Figure 12:
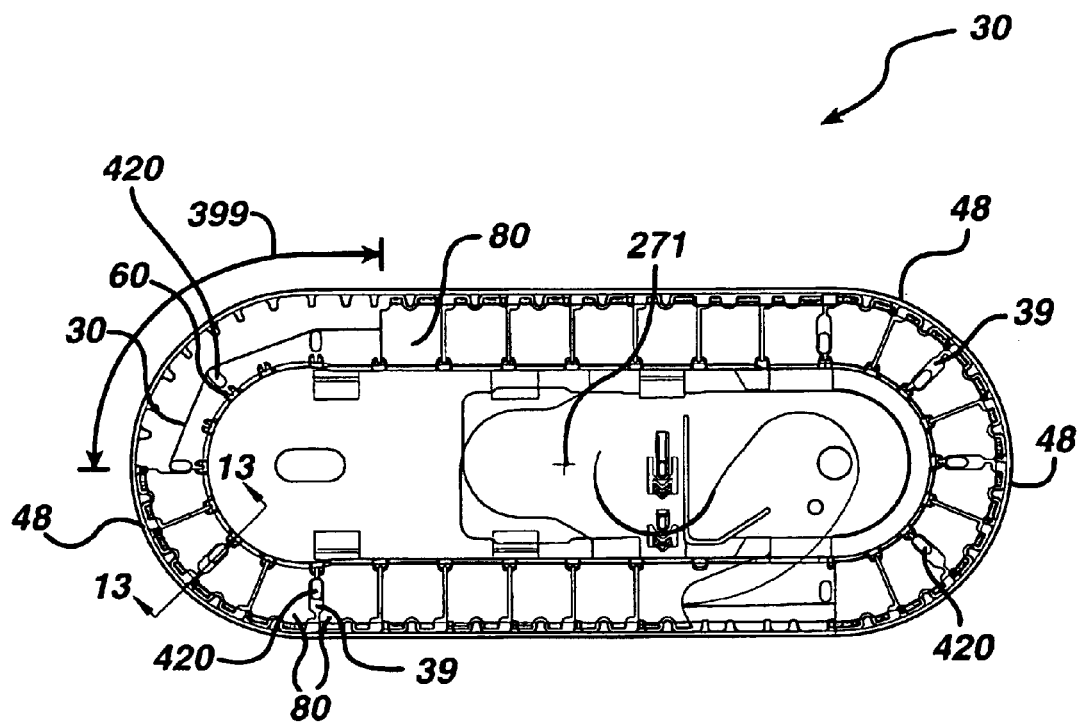
FIG. 12 is a plan view of a tray package adapted for use with the packaging machines of the present invention, partially cut-away to illustrating the suture channel of the package and channel winding pins.

Referring now to FIG. 12, the package 30 is illustrated after it has been wound but prior to withdrawal of the machine winding tooling. The illustration has a portion of the suture channel cover flaps 80 removed along the sweep of arrow 399 for visual illustration of the suture track therebeneath. Prior to the winding operation at winding station 370, as the upper tooling 391 descends on the package 30, a plurality of winding pins 420 are inserted into a matching plurality of holes 39 between hinged flaps 80 at the opposed curved ends 48 of the package 30, and into the suture channel 70 prior to winding. The bundle of wound sutures 30 is accumulated on the winding pins 420 as the winding operation proceeds. The insertion of the winding pins 420 into suture channel 70 prior to the rotational winding operation displaces the bundle of strands 30 away from the package suture track inner wall 60 a distance "X". Said suture bundle will be therefore loose after winding pin 420 withdrawal, a condition that enhances free suture dispensing by the user, particularly for relatively limp, multifilament suture material constructions. "Free suture dispensing" is a desirable package quality that refers to the ease with which the end user of the package can grasp the needle with suitable forceps and pull the entire suture length from the package, causing it to uncoil slidingly from the suture track with minimal friction.

Figure 13:
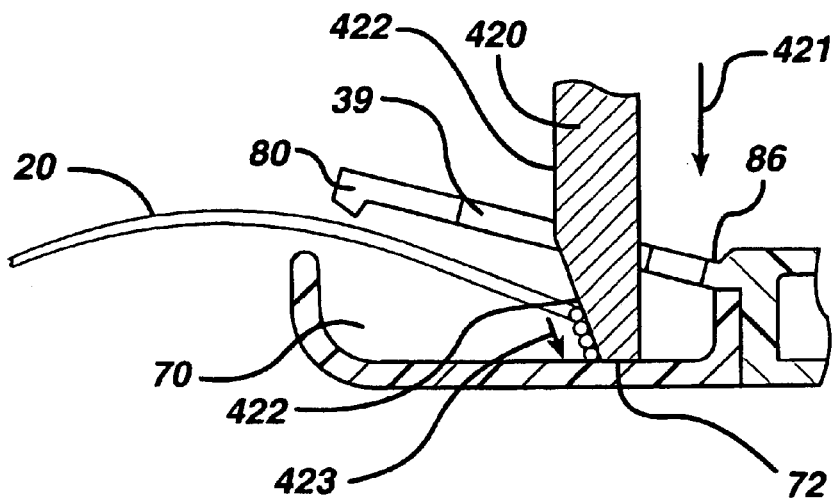
FIG. 13 is a magnified, cross-sectional view of the package of FIG. 12 taken along View Line 12—12, illustrating a channel winding pin of FIG. 11 in the suture channel during a suture winding operation.

Referring now to FIG. 13, the suture winding channel 70 is illustrated. The suture channel flap 80 is shown open position (i.e., displaced upwardly), pivotally raised upward by the winding stylus (not shown) about hinge point 86. At the start of the winding cycle, the winding pins 420 are thrust in the direction of arrow 421 until contacting the floor 72 of the suture channel 70. As the package is automatically wound it is rotatingly displaced about a vertical axis 271 as seen in FIG. 12. The suture strand 20 trailing from the needle 10 is fed into the suture channel 70 and bears against the tapered surface 422 of winding pin 420. Said winding pin embodies a tapered surface 422 that causes the suture strand to slide down said tapered surface, in the direction of arrow 423, the first loop of said suture strand coming to rest generally against the suture channel floor 72. As successive is winding loops of suture 20 are accumulated on the winding pin tapered surface 422 and slide down, an essentially linear array of loops suture 20 is formed above and in contact with the first loop of suture 20.

At the completion of the winding operation, closing of the flaps 80, and withdrawal of winding pins 420, the array of suture loops 20 thus formed tends to position the suture strand closest to the needle 10 toward the inner wall 60 of the suture channel 70, and the remaining loops of suture 20 sequentially outward therefrom. This resulting machine controlled arrangement of the suture loops 20 in the suture channel 70 of the package 30 enhances reliable and free dispensing of the suture 20 by the end user.

Figure 14:
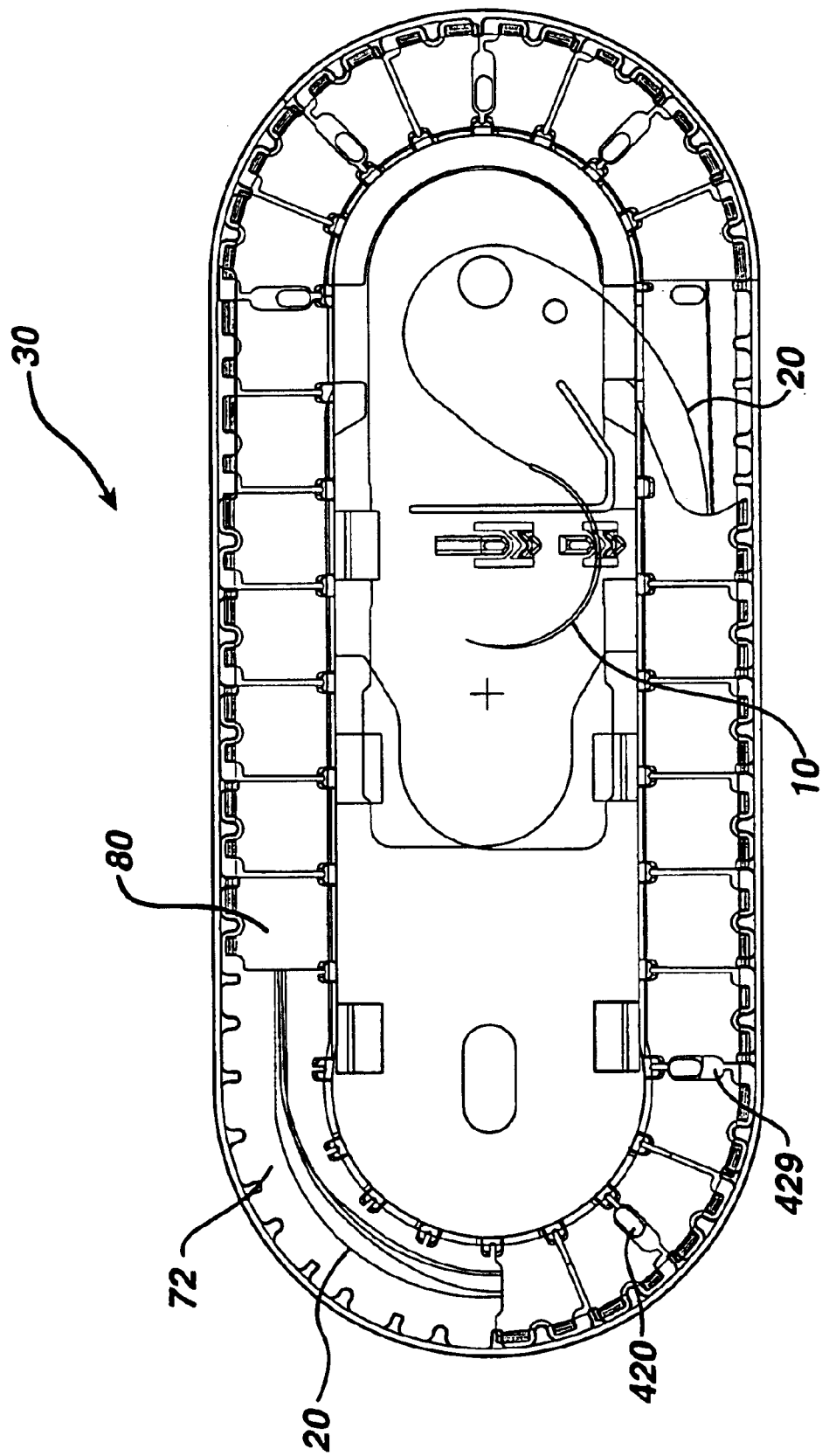
FIG. 14 is a plan view of the package of FIG. 2, having a partial cut-away illustrating the relaxation of the suture loops in the suture channel after channel winding pin removal.

The illustrated process takes place on all of the winding pins 420 during the winding machine sequence. When the machine tooling 391 subsequently withdraws the winding pins 420, the strands of suture 20 stay roughly as positioned in the suture channel 70, but relax to form a looser cluster as seen in FIG. 14.

Figure 15:
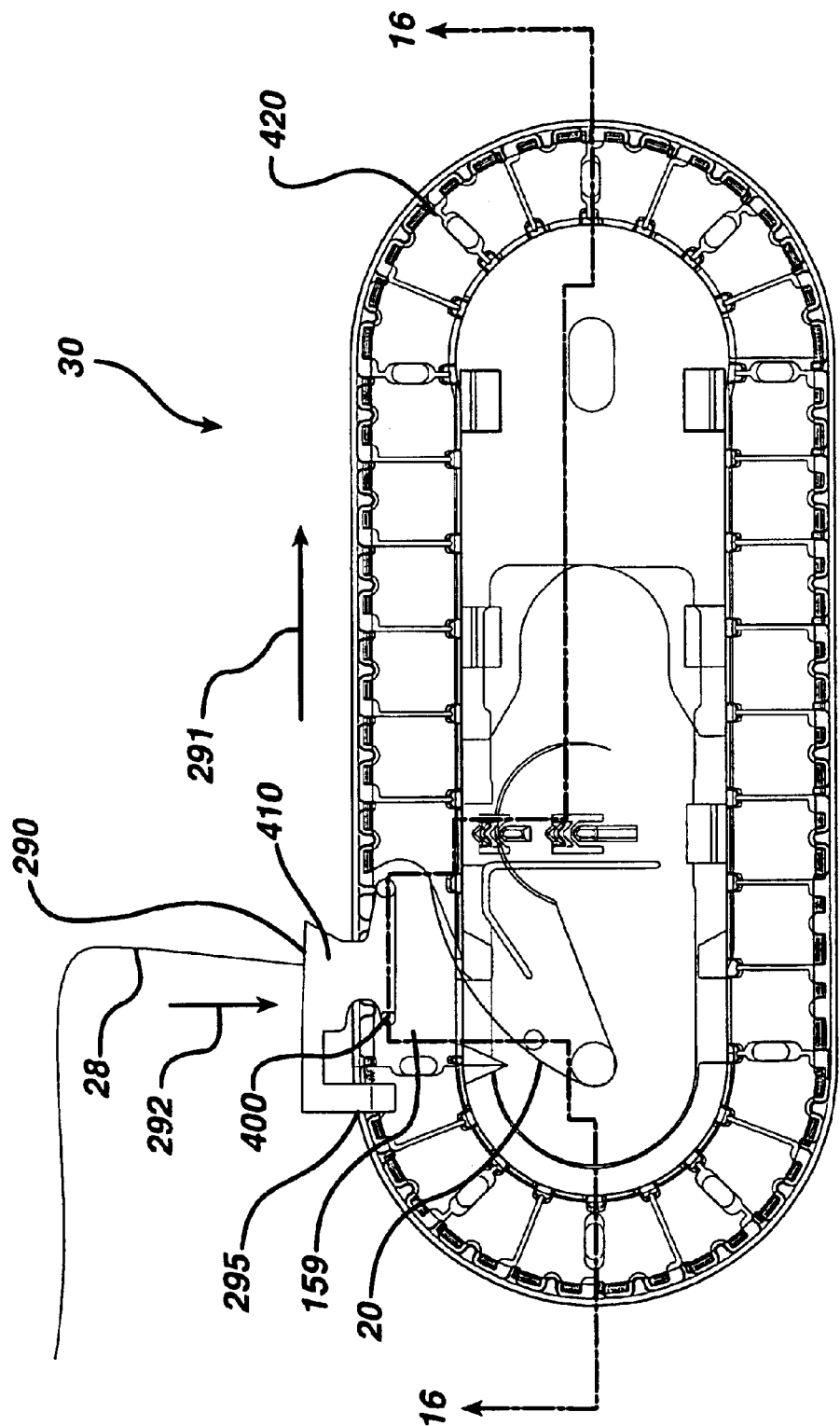
FIG. 15 is an illustration of a tray package having a suture channel, and having a stylus of the machine of the present invention inserted in the channel.
Figure 16:
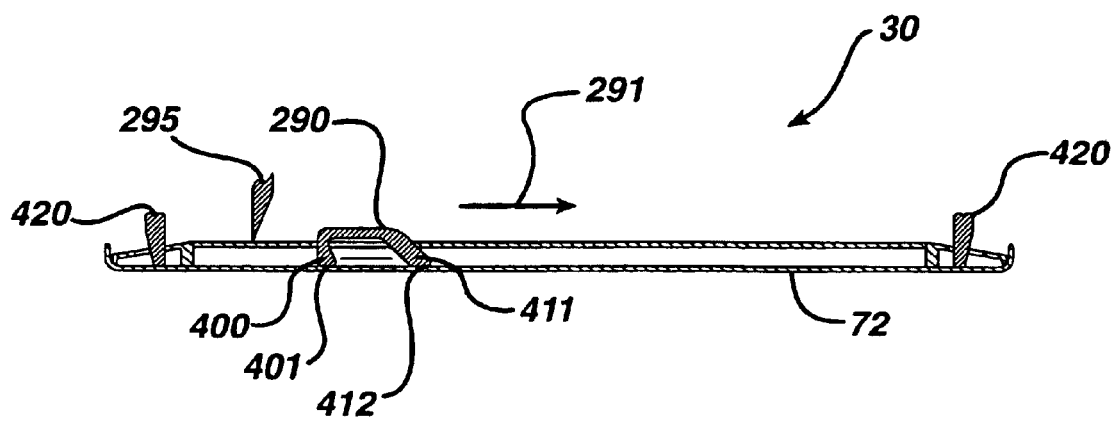
FIG. 16 is a side, cross-sectional view taken along View line 16—16 of the package of FIG. 15.
Figure 17:
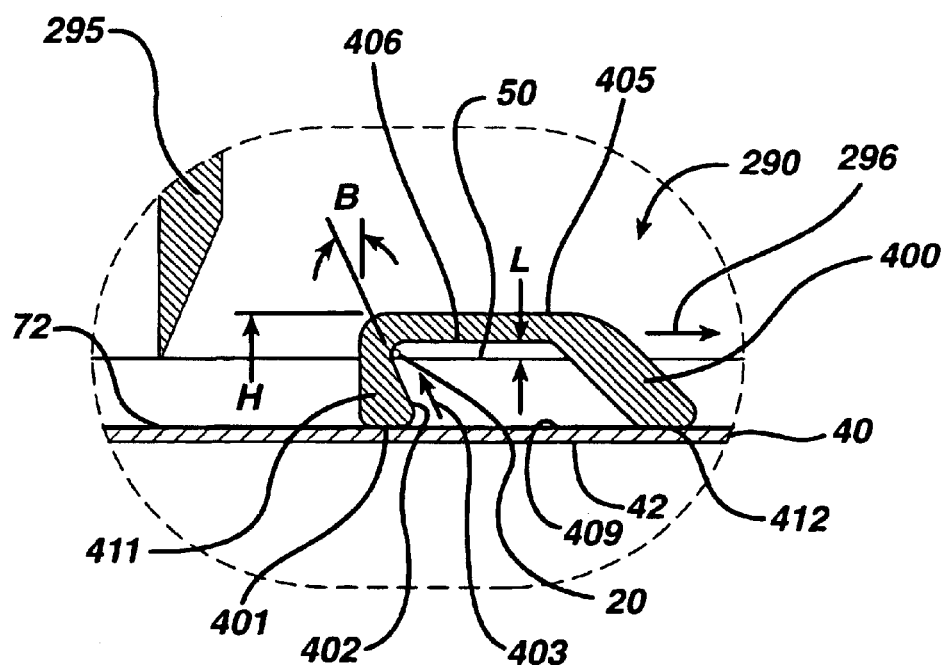
FIG. 17 is a magnified view of the package of FIG. 16, illustrating the stylus in the channel.

The operation of the winding stylus 290 is illustrated in FIGS. 15, 16, and 17. Referring first to FIG. 15, the winding stylus assembly 290 is seen moving, during the winding operation, in the direction of arrow 291 with respect to the tray package 30, winding a suture 20. As winding progresses, the remaining unwound suture 20 advances in the direction of arrow 292 with respect to the stylus 290. The suture strand 20 enters the stylus 290 and is guided by the stylus heel 400, under little tension, and gently laid into the suture channel 70 parallel to the outer channel wall 50, and distal to winding pins 420. On each lap around the suture track, the stylus 290 lays an additional suture strand 20 upon the sloping surface 422 of the winding pins 420 as illustrated in FIG. 13, and described in text associated therewith. The stylus 290 is located mechanically to dear the winding pins 420 sufficiently to not pinch or otherwise impart damage to the suture strand 20.

As seen in FIG. 16, the stylus 290 is illustrated sliding in the direction of arrow 291 on the suture track floor 72 with the nose 411 and heel 400 pressed with downward force of the stylus bottom surfaces 412 and 401 to bear thereon. The height H of the stylus 290 as seen in FIG. 17, is sufficient to effectively open the flaps for suture insertion, but minimized beyond that to reduce stress and potential permanent deformation of the hinges 86 of door members 80(See FIG. 4). The internal height L of the stylus ceiling 406 is greater than two suture diameters above the suture track outer wall 50 thereby eliminating pinching or mechanical interference that might damage the suture 20.

The heel member 400 has a suture guiding surface 402 The suture guide surface 402 is sloped backward with a positive angle B, to cause a suture strand 20 to climb upward in the direction of arrow 403 as it slides through said suture guide gap 409, minimizing scraping of the suture against the top of the suture track outer wall 50.

All surfaces of the suture stylus tool 290 are polished, free of surface irregularities, and shaped to avoid sharp edges, angles, or corners that could cause damage to the suture strands.

Also illustrated in FIG. 17 are stylus 290 and a door closing member 295 positioned therebehind, moving with the stylus in the direction of arrow 296, to bear onto and press down suture channel doors 80 that do not spring back to their original closed, resting position after being raised and opened during the suture insertion operation.

Figure 18:
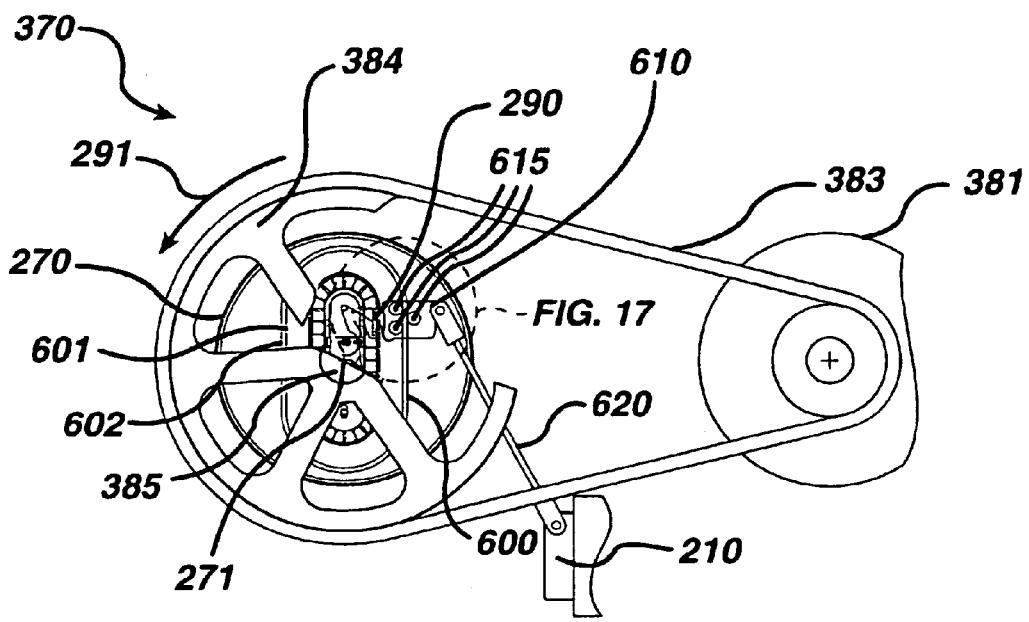
FIG. 18 is a plan view of the rotational and stylus components of the winding station of the packaging machine of the present invention.
Figure 19A:
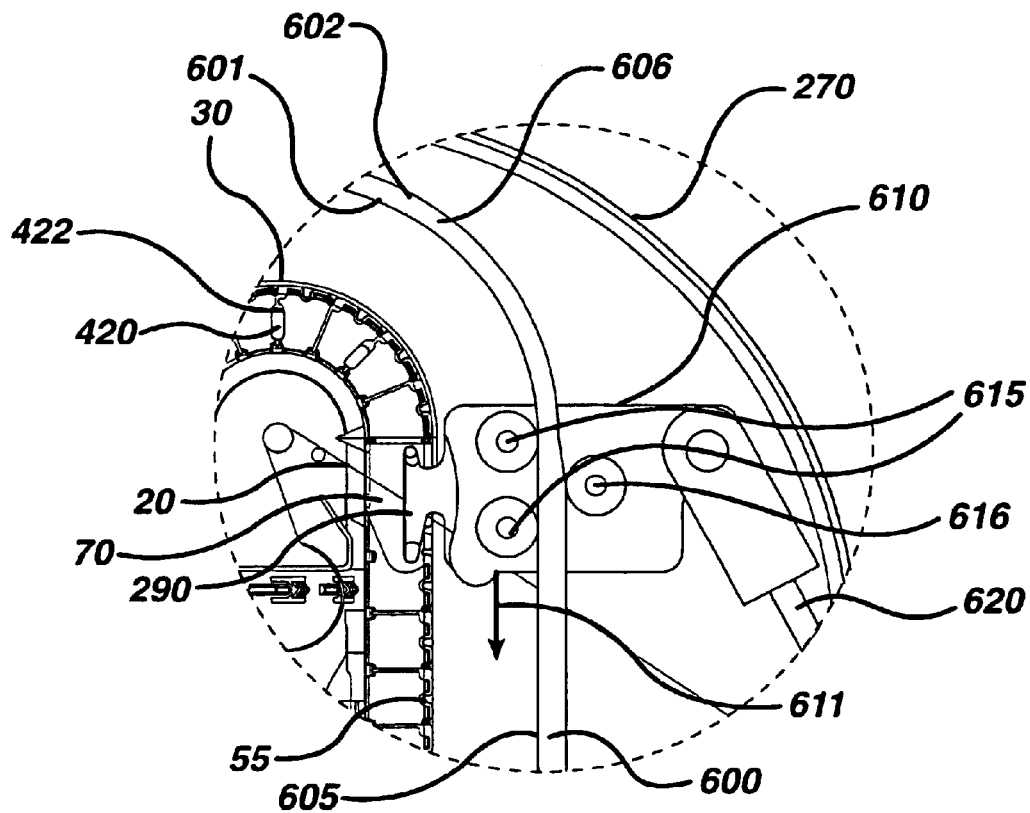
FIG. 19A is a magnified plan partial view of the stylus and package of FIG. 18.

The machine winding station 370 with sections of the drive hardware broken away to view portions of the package and stylus is seen in FIGS. 18 and 19A. The winding machine station 370 comprises a rotatable nest 270 and package tray 30 mounted therein. Said machine station further comprises a cam track 600, rotatable therewith, said cam track having a first or inner side 601, and a second or outer side 602. A stylus carriage 610 has the suture guide stylus 290 and a plurality of rollers 615 engaged with the cam track 600. Said stylus carriage is constrained by a rod 620 pivotally mounted at each end to said stylus carriage 610 and the machine frame 210 respectively. Said nest 270, package 30, and cam track 600 are torsionally integral and rotatably driven in the direction of arrow 291 by the motor 381, belt 383, pulley 384, and shaft 385, about the rotation axis 271. Referring to FIG. 19A, the inner profile 601 of the cam track 600 geometrically comprises a pair of opposing straight sides 605 and a pair of opposing semi-circular ends 606, so-configured and sized to form a surface essentially parallel to the package suture track 70. The stylus carriage 610, and the stylus 290 fixed thereon, moving relative to the package 30 in the direction of arrow 611, guided by the inner rollers 615 bearing on the inner surface 601 of the cam track 600, traces a path for the stylus 290 within the package suture track 70. Said path is between the suture track outer wall inner surface 55 and the outer surface 422 of the winding pins 420. Said path clears said outer wall 50 and winding pins 420 sufficiently to avoid pinching the suture 20. The relative motion of the stylus 290 in the direction of arrow 611 causes the nose member 411 and heel member 400, straddling the suture strand 20, to progressively advance around the periphery of the suture channel 70, sequentially plowing the suture channel cover flaps 80 open and threading the suture strand 20 therebelow. A trailing plow 295 (not shown) cams cover flaps 80 down afterward.

Figure 19B:
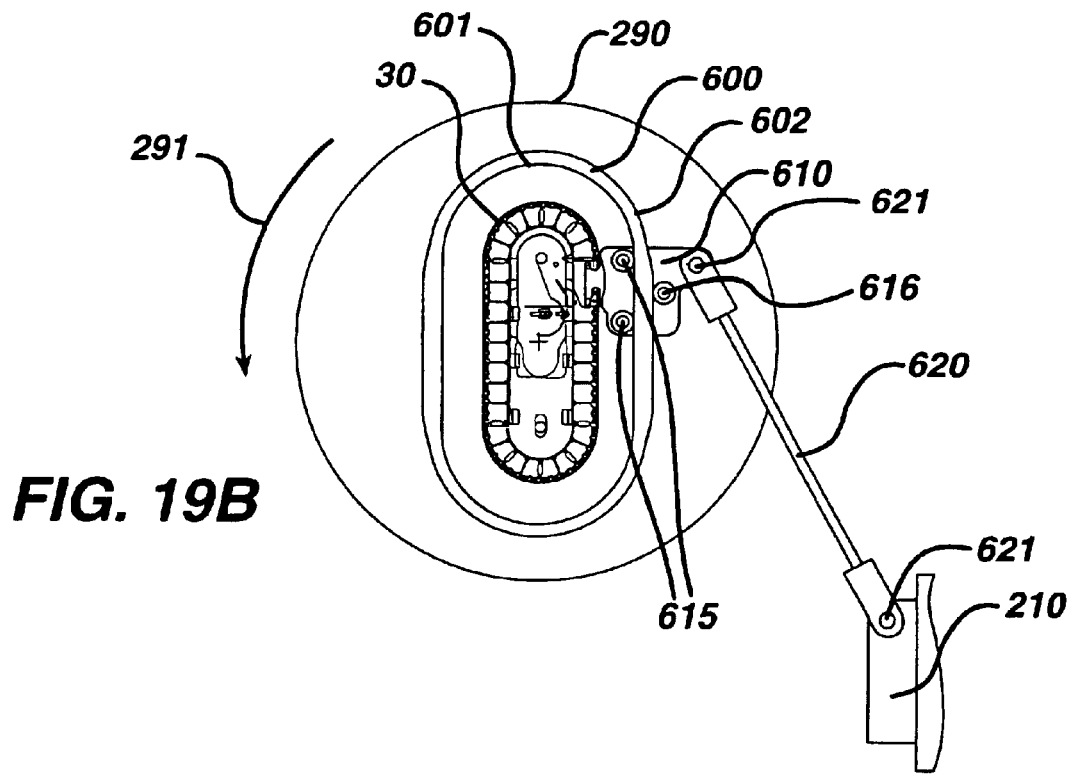
FIG. 19B is a plan view of the stylus guiding cam track and related mechanical components of the winding station of FIG. 19A.
Figure 19C:
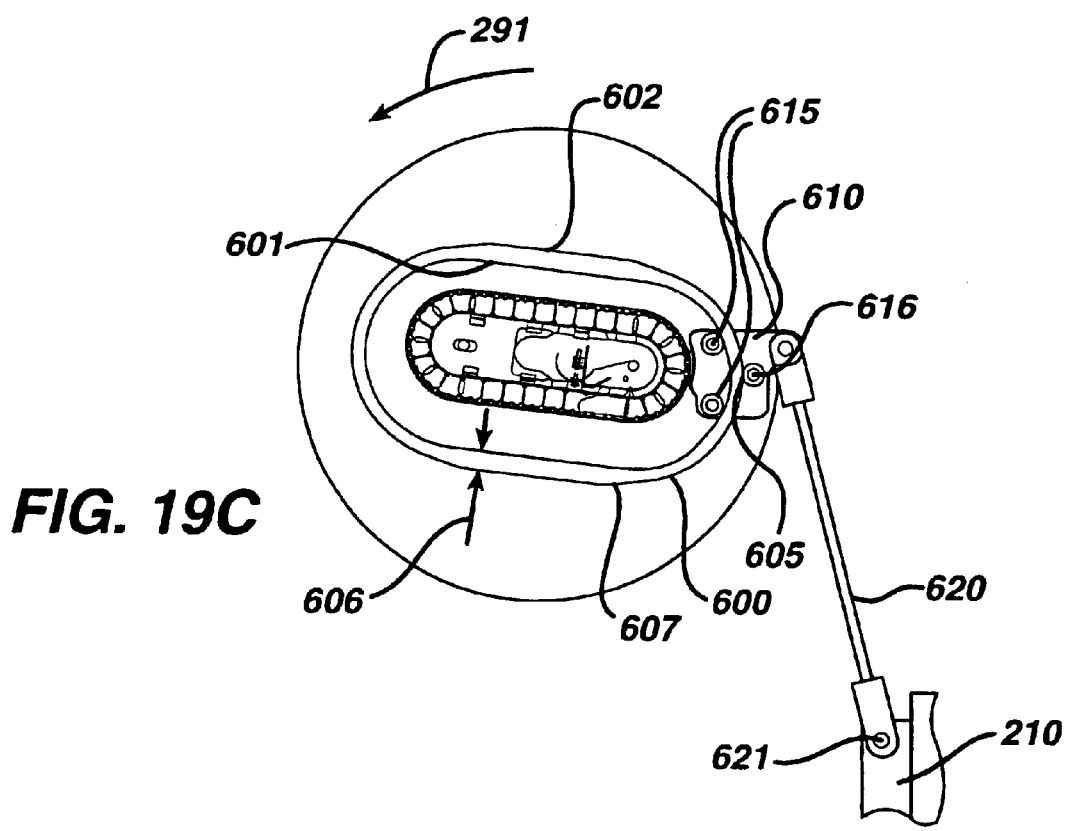
FIG. 19C illustrates the stylus guiding cam track and related mechanical components of FIG. 19B rotationally displaced during a winding operation.

Referring now to FIGS. 19B and 19C, the means of generating the relative motion and controlling the path of the stylus carriage 610 relative to the package 30 is illustrated. As seen in FIG. 19B, the nest 270, the package 30 integral thereon, and the cam track 600 are rotated in the direction of arrow 291 as described hereinabove. The stylus carriage 610 is constrained from rotating with the cam track 600 by the rod 620 and pin connection 621 thereon at the carriage end, and a similar pin connection 621 the machine frame 210. The carriage 610 is guided by the inner track rollers 615 bearing against the inner track profile 601. Contact of the inner rollers 615 against said inner track is assured by the backing roller 616 bearing against the outer track profile 602.

FIG. 19C illustrates the mechanism of 19B in partial angular displacement to further illustrate the cam track and stylus carriage rollers. The outer track profile 602 is sized and shaped to trace a locus of contact points 605 of the backing roller 621 as the inner rollers 615 follow the inner track profile 601, thereby maintaining a confined but free rolling contact of the carriage 610 with respect to the track 600 passing therebetween.

Said locus of points will define a track width 606 that is not parallel to the inner profile 601, but varies at the points 607 where the carriage rollers 615 and 616 transition from straight to curved sections.

It can be seen that the function of the inner track profile 601 is to guide the stylus 290 in the package suture channel 70, and the function of the outer track profile 602 is to maintain proper mechanical clearance and rolling contact of the inner rollers 615. It can also be seen that the outer and inner track functions could work equally well if reversed.

The winding rotation described hereinabove continues for a sufficient number of turns to insert the entire suture length 30 into the suture channel 70, and continue additionally until the stylus 90 is at the start position illustrated in FIG. 15. The winding tooling 390 is raised, and the turret 250 (FIG. 7) is indexed for the next operation.

Figure 20:
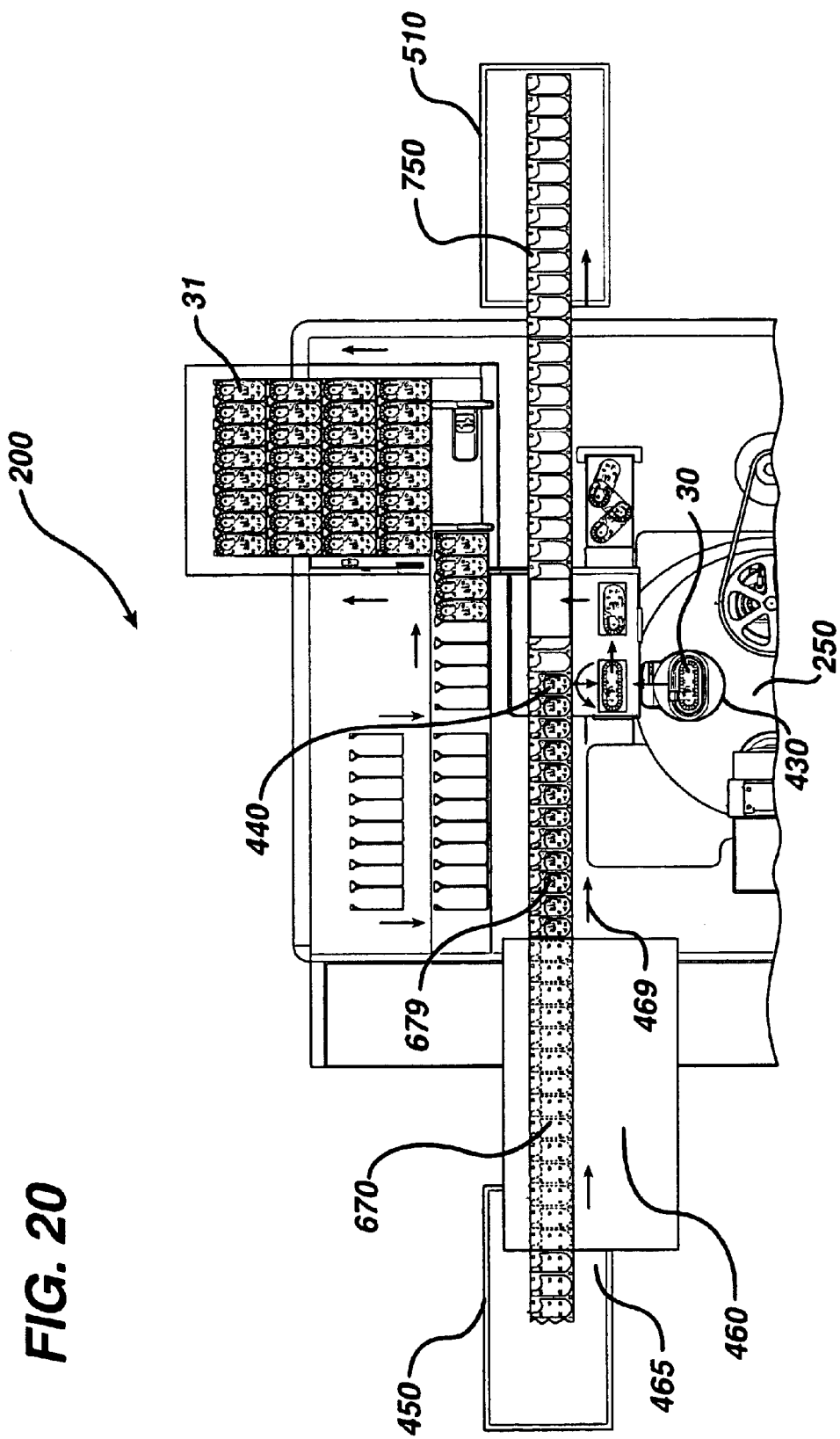
FIG. 20 is a detailed, plan view illustrating the winding machine top of FIG. 9.

Referring now to FIG. 20, transfer station 430 of turret 250 is seen after indexing from the winding station 370, with the tray package 30 containing wound suture 20.

The machine operations after winding take place utilizing transfers of the package 30 performed by slides and pick and place mechanisms. These devices may be actuated by air cylinders, lead screws driven by motors, servo or otherwise, and other techniques, utilizing vacuum cups or mechanical grippers to grip the product. These devices are custom designed, commercially purchased, or a combination thereof, and are known art in the machine design field. They are therefore not described in mechanical function, but by only the motion or product transfer that is made, recognizing that those knowledgeable in the design field would have a number of choices within the field of known art to accomplish the described function.

To complete the package assembly after winding, a cover panel 650 made of sheet material 640 is affixed thereto after first being printed with suitable label information. Said sheet material in the preferred embodiment is paper.

Figure 22:
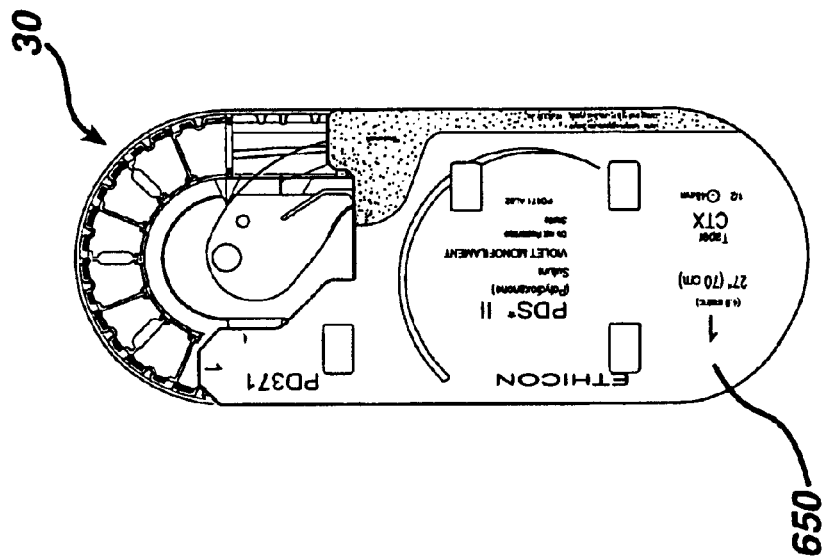
FIG. 22 is a plan view of the assembled suture package of FIG. 21, after assembly of a paper cover.
Figure 24:
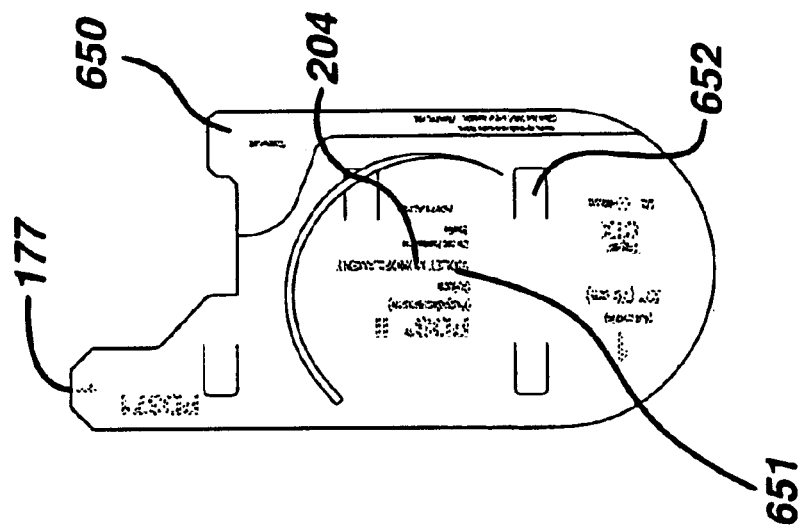
FIG. 24 is a plan view of the paper cover of FIG. 23 illustrating the cover after printing by the machine in-line printer.
Figure 23:
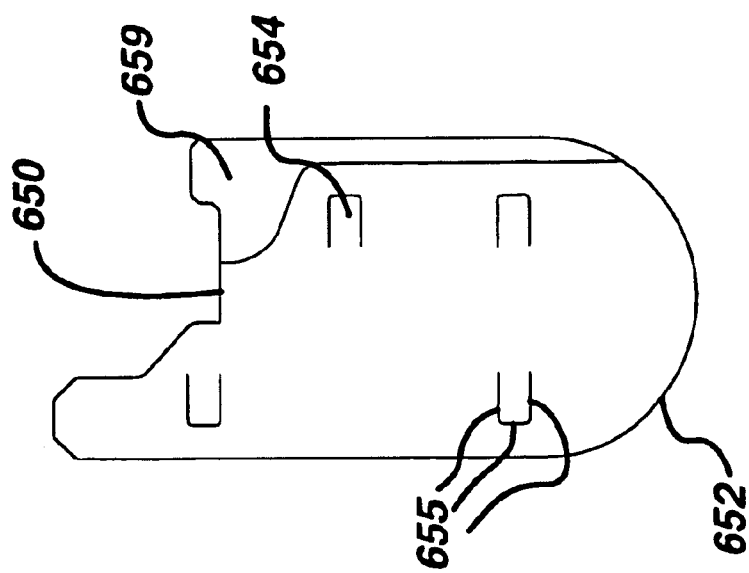
FIG. 23 is a plan view of a paper cover prior to printing by a machine in-line printer, illustrating the staking tabs die-cut therein.

Referring to FIGS. 21 through 24, the package tray 30 is seen prior to cover 650 placement at station 430. The needle 10 is seen contained the needle park 100 and the suture strand 20 coiled into the suture channel 70. FIG. 24 illustrates the paper cover 650 with label information 651 printed thereon. FIG. 22 illustrates the completed package of FIG. 21 with the printed cover 650 attached thereto. The cover 650 is seen to have an outer periphery 652 shaped to conform to the package 30 outer shape, a plurality of die cut tabs 654 lanced on three sides 655, and a printed color band 659, which is common to the label for many suture products. FIG. 24 illustrates the paper cover 650 of FIG. 23 that has added printed information 651 unique to individual suture products, and therefore one particular production lot. This is referred to as the 'variable information' because it must be varied or changed often; each time the machine is set-up to package a different suture product or production lot. The function of the printer on the machine is to custom print the variable label information, from an easily changed electronic database, for each machine cycle, thereby eliminating the need to change the supply of paper covers when the machine is changed to run a different product. It can be seen that changing the supply of paper covers 650 with each machine product changeover would be required if they were conversely pre-printed off-line, resulting in waste, handling damage, mechanical feeding and hoppering complexities, consumption of time, contamination, increased inventory, and possible product mix-ups.

Referring now to FIGS. 25 and 26A, the paper cover supply system of the packaging machine 200 is fed with a strip 670 of pre-cut and color printed covers 650 as illustrated on the left hand side 461. The strip 670 is indexed from left to right as indicated by arrow 671 as the machine cycles, through the printer 460, illustrated not to scale, exiting the printer 460 on the right side 462. The strip 670 is preferably out-sourced or manufactured in a separate high volume operation, and brought to the packaging machine in bulk roll or fan-fold stack. The strip 670 is seen to have a repeat pattern of die-cut shapes 680. The die-cut line 682 on the periphery 652 of the cover 650 severs the cover 650 from the strip 670 except in a plurality of tie points 683. The tie points 683 are narrow areas where the peripheral cut 682 is interrupted, and are dimensioned to be sufficiently strong to hold the cover 650 in the strip 670 during feeding, but sufficiently small in cross section to allow it to be separated and stripped out mechanically. The strip 670 is seen to additionally have a plurality of die-cut tabs 654, positioned dimensionally to coincide with tab receiving pockets 130 (See FIG. 21). The strip 670 also has a printed color band 659, and a printed bar code 656 which contains information identifying the particular printed color, thereby allowing the machine control system to read the bar code and verify the correct label color for the particular product being run. The strip 670 further comprises a plurality of pilot holes 675 dimensionally registered with the die-cut cover pattern and the printed color band and barcode.

Those familiar with typical commercial converting operations will recognize that the features of the cover strip 670 can be manufactured with high speed, low cost converting press operations, thereby allowing a continuous strip on a large roll or fan-fold stack to be economically supplied to the packaging machine 200.

Referring now to FIG. 20, the cover strip 670 is supplied from a container 450 at the infeed area 465 of the printer 460. FIG. 20 illustrates the cover strip 670 passing through the printer 460 in the direction of arrow 469 and emerging with printed information 651.

Continuing reference to FIG. 20, the machine 200 has a printer 460 that feeds the strip 670 to print the variable information 651 as seen in FIG. 24. A number of commercial printer technologies are available for this application. The preferred embodiment utilizes a digital thermal transfer printer that accepts a downloaded digital image database for the printed graphics. The printer comprises internal feed rolls (not shown) that advance the strip 670 into the printer 460 and register the image printed thereon in dimensional registration with the paper strip pilot holes 675. A solid optically detectible target 677, as seen in FIG. 25, is also printed, and sensed with a suitable mounted electronic photoelectric device (not shown) to verify that the printer 460 is functioning and the image has been printed.

The thermal transfer printer 460 operates on the principle (not illustrated) of a print head comprising an array of micro heating elements in contact with an ink ribbon passed therebelow. The thermally activated ink transfers pixel sized dots or marks to the paper passing said print head and ribbon in accord with a digital image signal received from a PC computer suitable connected to the machine. To set up the printer 460 at the beginning of production run, an operator scans a bar code from a production form, or manually types in a code, which orders the download of the label artwork from a database electronically filed in the computer memory. A slack loop section 679 (See FIG. 20), in the paper strip 670 exiting the printer is maintained to allow the printer internal strip feed stroke to be non-synchronized with the winding machine mechanical feed stroke for the strip.

The paper strip 670 for the printing and cover placement functions described hereinabove require a precise, repeatable registration means for die cutting the cover shape, printing the variable information, and feeding to the assembly station of the machine. It also requires a cost efficient use of paper raw material, said efficiency relating to the quantity of paper consumed by the process compared to the quantity of paper covers produced.

Figure 26C:
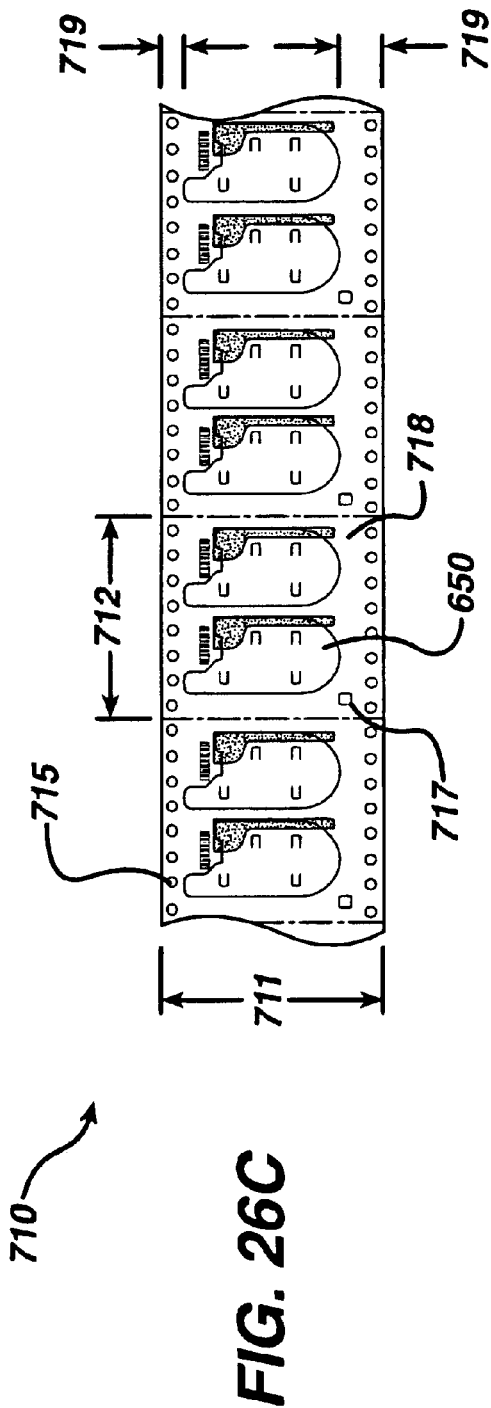
FIG. 26C is a plan view of a paper cover strip having a sprocket feed approach for a rotary converting press.

FIGS. 26B and 26C illustrate conventional paper strip layouts for a commercial converting process whereby the paper strip is roll fed through the high volume rotary printing and die cutting press in the direction of arrow 690.

FIG. 26B illustrates a common strip layout 700 of typical width 702 and multiple die cut covers 650 therein. The covers 650 are subsequently removed from the strip 700 and used on the packages 30. This design is less efficient in paper use due to the relatively large scrap area 705 remaining after the covers 650 are removed, and there is no feature for subsequent accurate registration through the packaging machine printer and assembly station. The covers 650 have to be handled and automatically fed as individual pieces. FIG. 26C illustrates a strip design 710 that meets the means of registration requirements by providing sprocket holes 715 for the feeding system on the packaging machine. Further registration means is provided by a required square hole 717 configured for optical detection by the packaging machine printer. The embodiment illustrated in FIG. 26C comprises a repeating panel width 712 of two paper covers 650 each. The strip layout is less efficient due to the relatively large scrap area 718 required beyond the basic cover width 711 for the sprocket hole tracks on the strip edges 719.

Figure 26D:
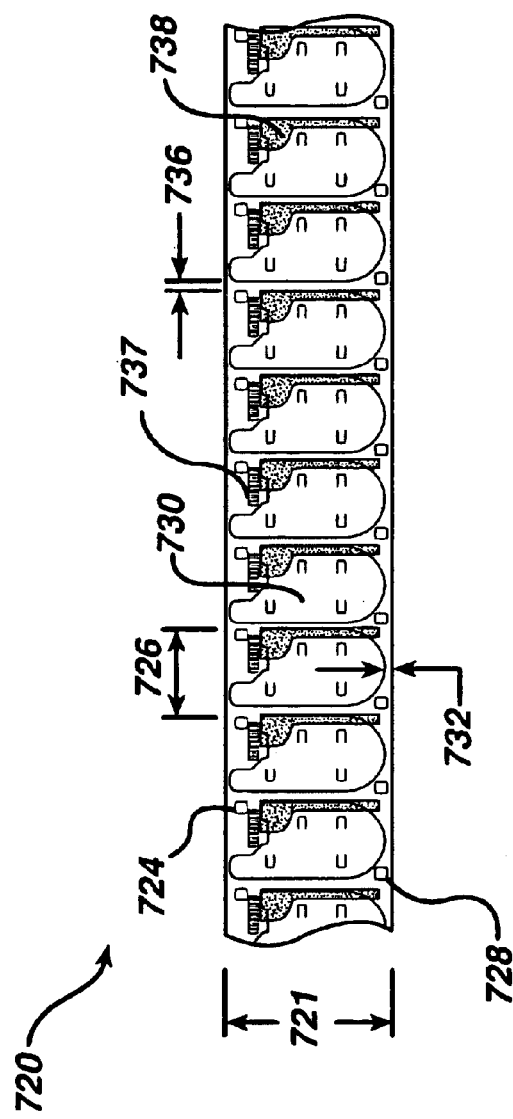
FIG. 26D is a plan view of a preferred embodiment of a paper cover strip useful with the packaging machines of the present invention, illustrating design features to minimize paper waste.

The preferred embodiment, illustrated in FIG. 26D, comprises a strip 720 that uses the required square printer registration holes 724 to also serve as mechanical feed holes for a linear feeder, designed to allow the holes to be on a larger pitch 726 than a sprocket feeder. Mechanical feeding is enhanced by addition of a square hole 728 on the opposing side of the strip 720. Said square holes are off-set from the paper cover die cut shape 730 thereby requiring minimal width 732 of scrap paper. The resulting layout is efficient in paper use due to the narrow strip width 721 made possible by elimination of sprocket holes, and the more dense positioning of paper covers 650 with minimal scrap paper 736 therebetween. The strip design of 26D includes a printed bar code 737 used to identify the printed color 738.

Feeding the paper covers 650 from the printed strip 670 (See FIG. 27) illustrates the cover strip 670 comprised of printed covers 650 therein, and the separation therefrom of the printed cover 650 by the cover punch mounted therebelow, punching in an upward direction, represented by arrow 740. The strip scrap skeleton 750, comprised of open gaps 752 where the covers 650 were extracted, exits the machine. The cover punch represented by arrow 740 is located at the cover feed station 440 as seen in FIG. 20. FIG. 20 further illustrates the strip s scrap bin 510 and the scrap strip 750 collected therein. Referring again to FIG. 27, the strip 670 is indexed linearly through the machine in the direction of arrow 671 by a walking beam motion device (not shown) that alternately inserts carriage mounted pilot pins 678 into the upper and lower strip registration or pilot holes 675 and advances said strip 670 one cover pitch in distance with each machine cycle. Location accuracy of printing, the die cut cover shape, and assembly vacuum gripper on the paper cover is maintained because these locations are all dimensionally registered to the same pilot holes 675.

Figure 31:
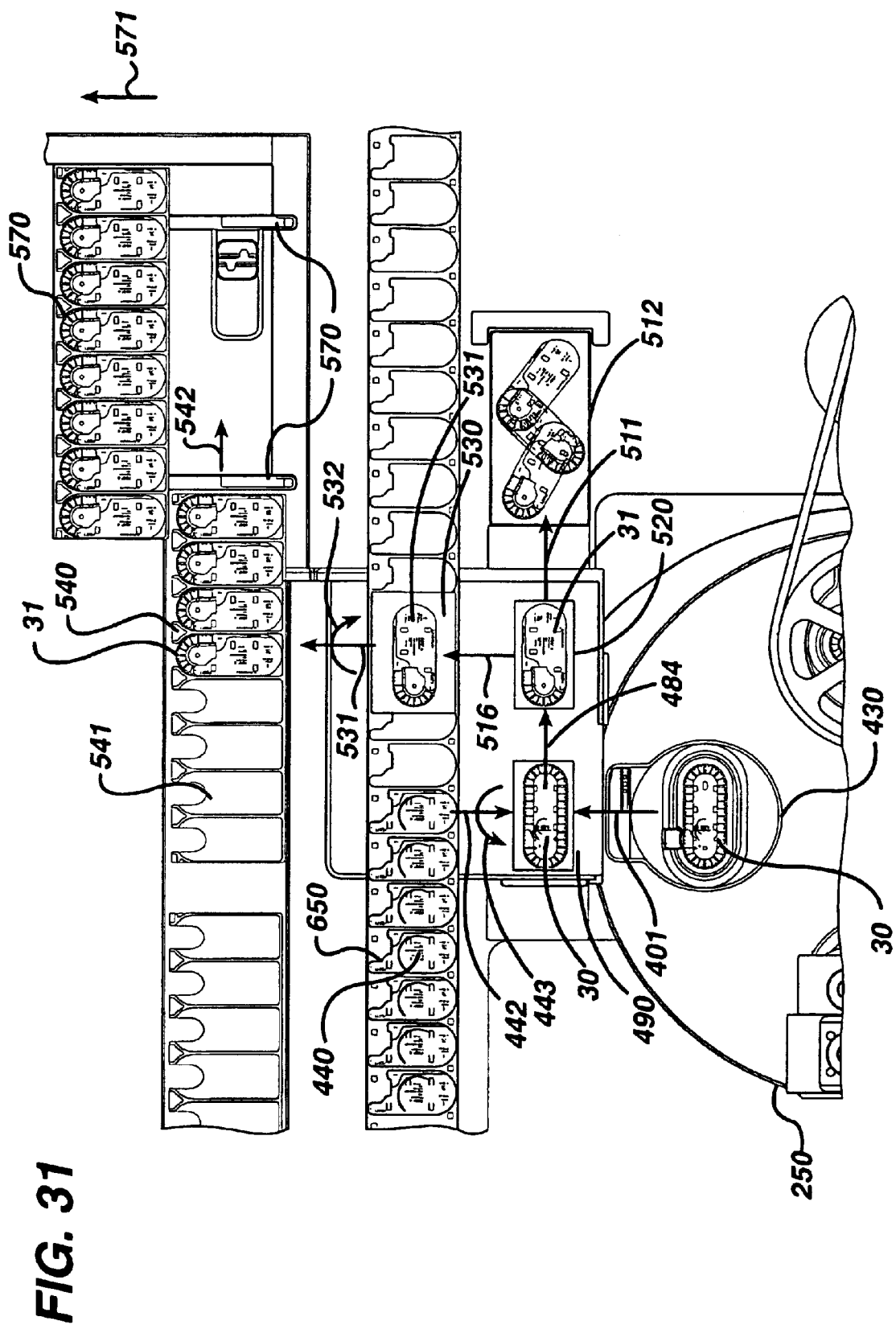
FIG. 31 is a partial, magnified plan view of the machine of FIG. 20, illustrating the machine operation for package completion and off-load.

Referring now to FIG. 31, the machine turret 250, after completion of the winding cycle described hereinabove, indexes rotationally 90° counterclockwise, thereby transporting a package tray 30 to the transfer station 430. Said package tray 30 is in the assembly stage as seen in FIG. 2, having a needle and suture assembly 5 mounted and wound therein.

Figure 27:
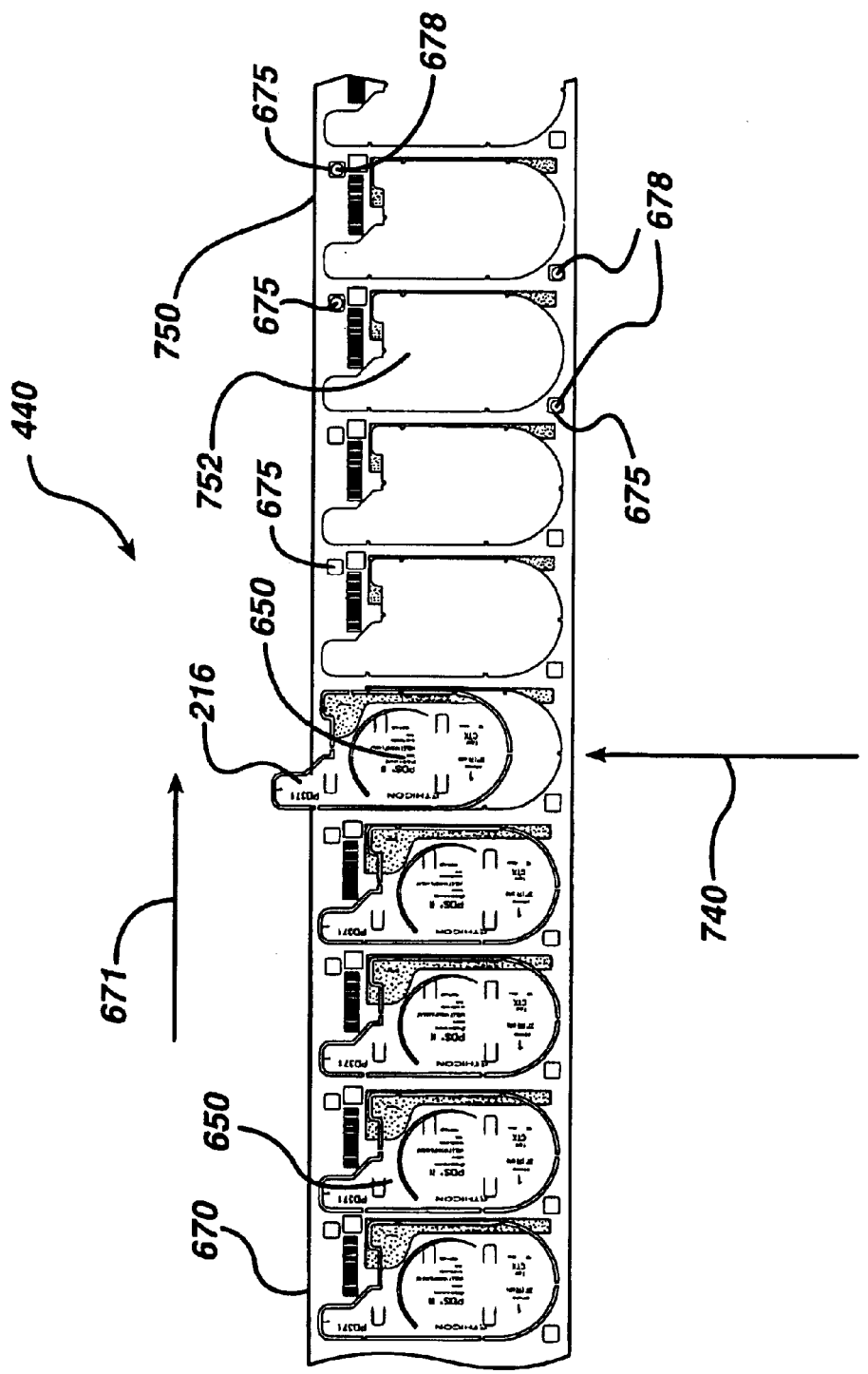
FIG. 27 is a plan view of the printed paper strip of FIG. 25, illustrating a cover punched-out from the strip at the machine cover feed station, and the processed strip with openings remaining thereafter.

Continuing reference to FIG. 31, a pick-and-place device with a vacuum cup equipped pick-up head (not shown) descends upon the package tray 30, grips, and transfers same, indicated by arrow 401, to the cover assembly station 490 of the machine. Said pick-and-place device has a second vacuum pick-up head (not shown) positioned over the paper cover punch-out and feed station 440. Said second vacuum pick-up head descends to said feed station 440 and vacuum grips the printed cover 650 as seen in FIG. 27, which is released from the carrier strip 670 by a stripping punch (not shown) therebeneath. Said second vacuum pick-up head elevates and linearly transfers said printed cover 650 in the direction of arrow 442, simultaneously rotating 90° counterclockwise as indicated by rotation arrow 443. Said second vacuum pick-up head lateral motion stops above the cover assembly station 480 and descends, depositing the cover 650 onto and aligned with the package tray 30.

Figure 21:
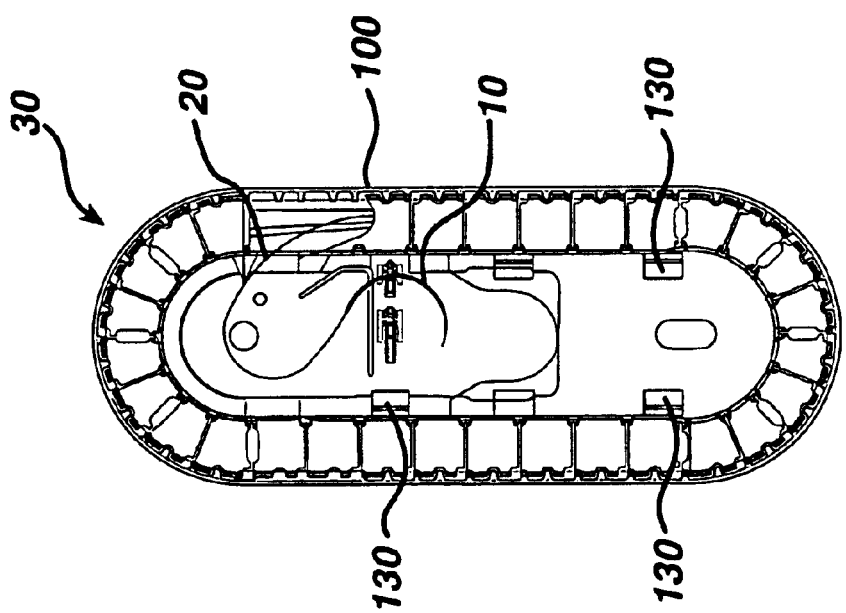
FIG. 21 is a plan view of an assembled suture tray package containing a surgical needle and suture prior to assembly of a paper cover.

Referring now to FIGS. 21, 22, 23, and 24, the cover 650 seen in FIG. 24, is placed over the tray 30 seen in FIG. 21, and aligned so that the plurality of lock tabs 654 are centered over the matching lock pockets 130. FIG. 22 illustrates the completed assembly 31 of tray 30 loaded with needle and suture assembly 5 after installation of cover 650.

Figure 28:
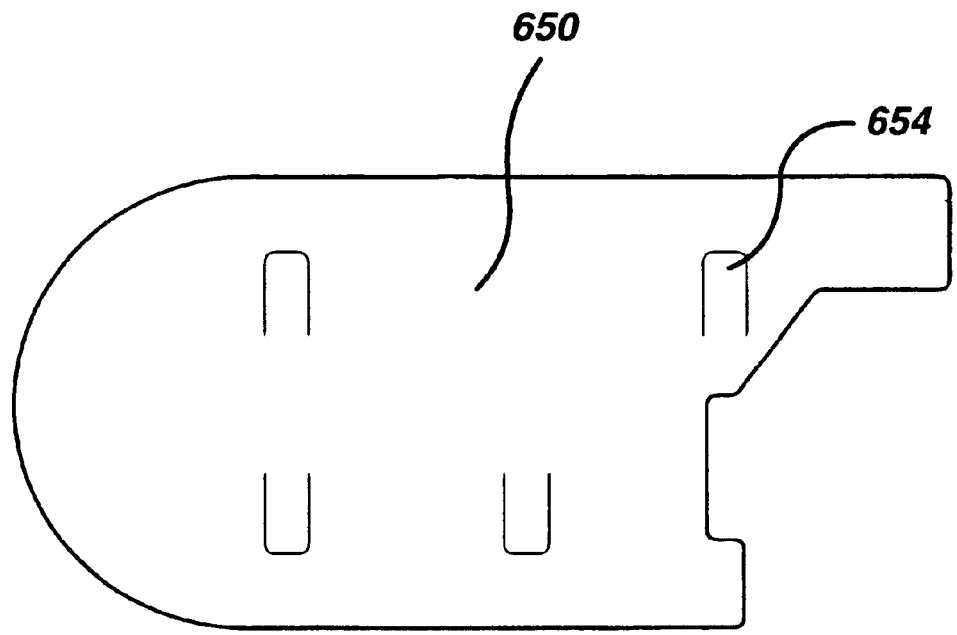
FIG. 28 illustrates a paper cover prior to staking onto a package.
Figure 29:
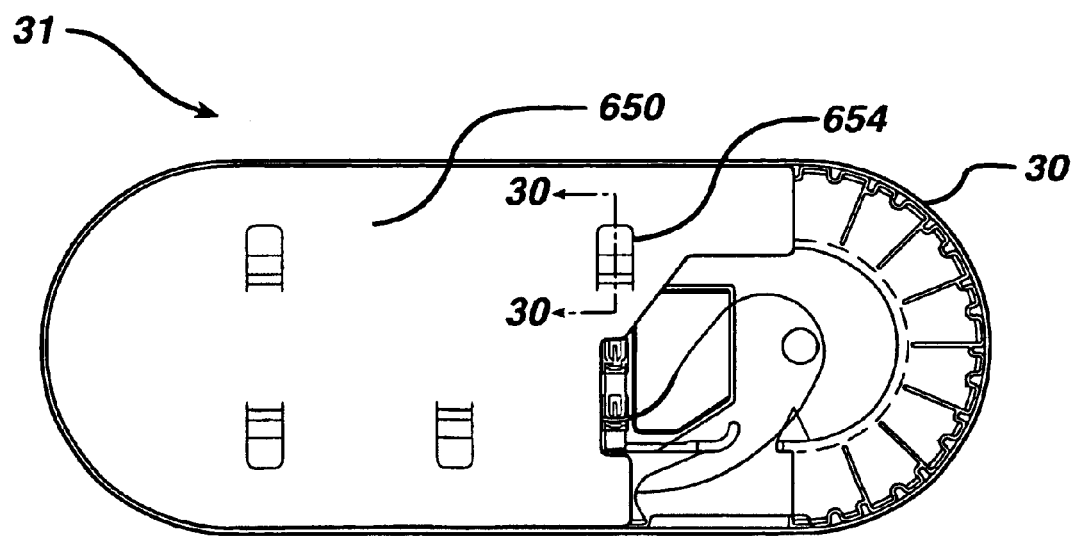
FIG. 29 illustrates the paper cover of FIG. 28 after staking onto a package.
Figure 30:
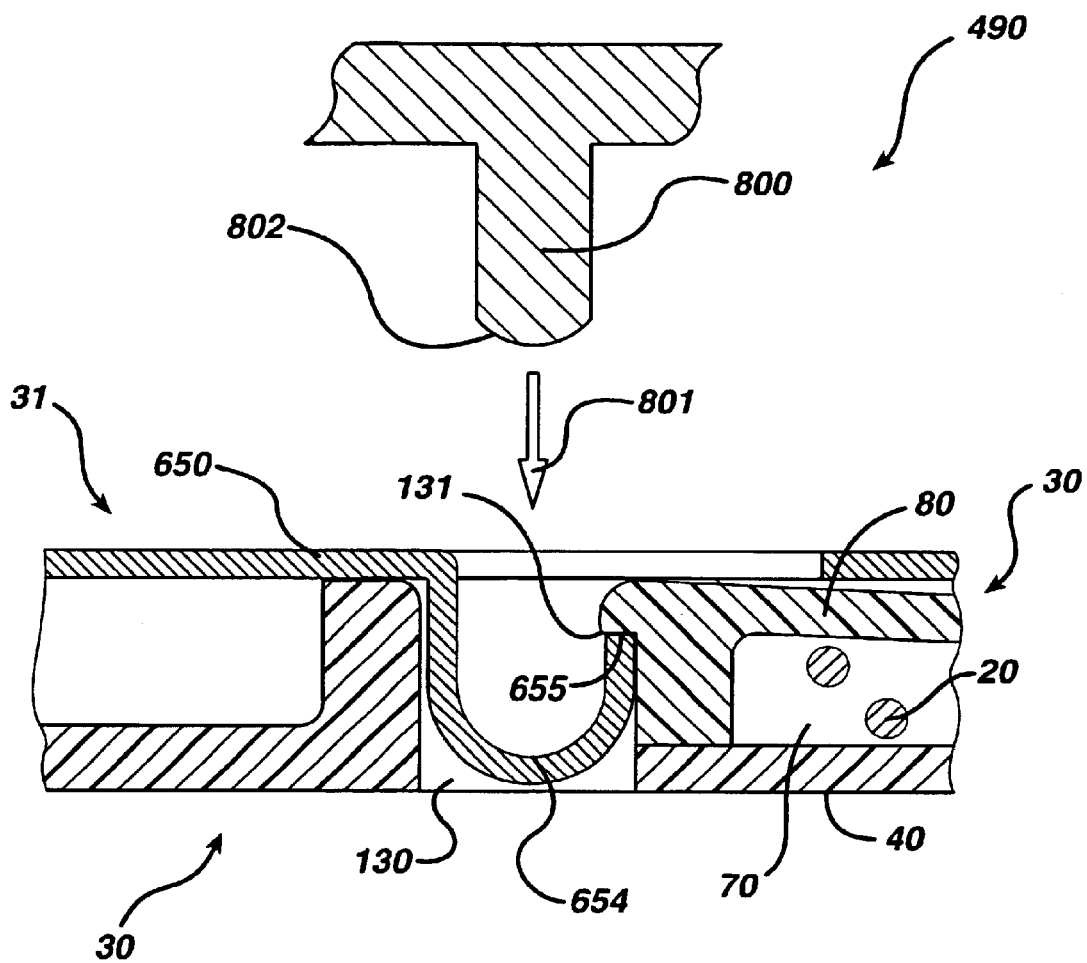
FIG. 30 is a side, partial cross-sectional magnified view of the package of FIG. 29 taken along View Line 30—30 illustrating the staking tab function and features.

FIGS. 28 and 29 illustrate a plan view of the cover 650 and of the package 30 after cover assembly to form the package and cover assembly 31. The printed information on the cover is omitted from this illustration for visual clarity. The cover 650 is attached to the tray 30 by staking a plurality of die cut paper tabs 654 into molded pockets 130 in the tray 30 utilizing the following process. Referring to FIG. 30 illustrating an enlarged section 30—30 of FIG. 29 through the staked paper tab 654, a plurality of staking tools 800, one only illustrated, positioned above each of the paper cover tabs 654, descend downward, as indicated by arrow 801, causing the radiused nose 802 to deform the die cut paper tab 654 into an inverted U shape, and form down into the tray pocket hole 130 until the tab end 655 has snapped past and sprung under the molded shelf 131, thereby securing said tab 654. The plurality of tabs 654, latched in this manner, secure the paper cover 650 to the tray 30. Precise function of every paper tab 654 latching under the shelf 131 is not necessary to retain the cover 650 to the package 30. Deforming the tabs 654 into the molded holes 130 is usually adequate, although every tab 654 may not be latched.

Referring now to FIG. 31, after the cover 650 is installed and staked to the package in the assembly station 490, a lateral shuttle device (not shown) transports the completed package assembly 31 as indicated by arrow 484 to the accept/reject station 520. The package assembly 31 may be rejected and pushed in the direction of arrow 511 into the reject bin 512 if signals indicating defective assembly in the earlier operations have been detected and received by the machine electronic controller (not shown). If the package assembly 31 in the accept/reject station 520 does not have associated defects in assembly, it is transferred in the direction of arrow 516 and placed on an intermediate station or demagnetization station 530. The package assembly 31 therein is exposed to a demagnetizing head (not shown). On the following machine cycle, a pick-and-place device (not shown) transfers the package assembly 31 in the direction of arrow 531, simultaneously rotating same 90° clockwise as indicated by arrow 532, lowering and loading same into the magazine hopper tray 540. The magazine hopper tray 540 contains stacks of accepted package assemblies 31 in the magazine hopper cavities 541.

The magazine hopper tray 540 is indexed linearly in the direction of arrow 542 progressively until all tray cavities 541 are filled. Filled magazine hopper trays 540 are subsequently moved in the direction of arrow 571 by the completed tray advancer 570 to a table surface of sufficient area to contain a plurality of filled magazines 540 thereon, to be off-loaded as completed product Although this invention has been shown and described with respect to detailed embodiments thereof, it will be understood by those skilled in the art that various changes in form and detail thereof may be made without departing from the spirit and scope of the claimed invention.

We claim:

1. A machine for winding suture into a suture tray package comprising:
   a machine frame having a top, a bottom, sides and an interior;
   a disc member rotatably mounted to the top of the frame, said disc member having a periphery, top, a bottom and a side about the periphery of the disc member;

a plurality of tool nests, each tool nest rotatably mounted to the top of the disc member, said tool nests comprising:
a nest frame, having a top, a bottom and sides; and,
at least two winding pin members extending up from the top of the nest frame;
a rotatable tool mounted to the machine frame, said tool being displaceable downwardly to engage with the pin members on the nest frame, such that rotation of the tool will rotate the tool nest, wherein said rotatable tool has a top and a bottom;
a plurality of channel winding pin members extending down from the bottom of the rotatable tool;
a cam track member extending down from the bottom of the rotatable tool, said cam track member having a pair of opposed longitudinal sides and a pair of opposed curved ends connecting the longitudinal sides, said cam track member having a first width along the longitudinal sides and a second width along the curved ends, wherein the first width is greater than the second width; and,
a stylus member movably mounted to the machine frame, for cooperation with the tool nests, comprising:
a stylus frame having a top, sides and a bottom;
a stylus mounted to the bottom of the stylus frame having a front nose member and a rear heel member separated by a suture opening, said stylus having a top surface; and,
a door closing member extending down from the bottom of the stylus frame adjacent to the stylus,
wherein the stylus member operatively engages the cam track member.

2. The packaging machine of claim 1, additionally comprising:
an in-line printer associated therewith for printing package covers; and,
a punching apparatus for punching printed covers from a printed strip of cover material.

3. The packaging machine of claim 2, additionally comprising an apparatus for receiving a printed cover from the punching apparatus, and mounting the cover to the top of a tray package.

4. The combination of a suture tray package and a packaging machine, comprising
I. a packaging machine comprising:
a machine frame having a top, a bottom, sides and an interior;
a disc member rotatably mounted to the top of the frame, said disc member having a periphery, top, a bottom and a side about the periphery of the disc member;
a plurality of tool nests, each tool nest rotatably mounted to the top of the disc member, said tool nests comprising:
a nest frame, having a top, a bottom and sides; and,
at least two winding pin members extending up from the top of the nest frame;
a rotatable tool mounted to the machine frame, said tool being displaceable downwardly to engage with the pin members on the nest frame, such that rotation of the tool will rotate the tool nest, wherein said rotatable tool has a top and a bottom;
a plurality of channel winding pin members extending down from the bottom of the rotatable tool;
a cam track member extending down from the bottom of the rotatable tool, said cam track member having a pair of opposed longitudinal sides and a pair of opposed curved ends connecting the longitudinal sides, said cam track member having a first width along the longitudinal sides and a second width along the curved ends, wherein the first width is greater than the second width; and,
a stylus member movably mounted to the machine frame, for cooperation with the tool nests, comprising:
a stylus frame having a top, sides and a bottom;
a stylus mounted to the bottom of the stylus frame having a front nose member and a rear heel member separated by a suture opening, said stylus having a top surface; and,
a door closing member extending down from the bottom of the stylus frame adjacent to the stylus,
wherein the stylus member operatively engages the cam track member; and
II. a suture tray package having a top and a bottom, the tray package comprising:
a flat base member having a top and an outer periphery;
an outer wall extending up from the base member about the periphery of the base member;
an inner wall, interior to the outer wall, extending up from the top of the base member, said inner wall having a top and said inner wall spaced away from the outer wall to form a suture channel;
a plurality of door members extending from the top of the inner wall over the winding channel, each such door member having a proximal end and a distal end, and opposed sides;
a plurality of openings between at least some of the door members for receiving channel winding pin members; and,
at least two needle park members extending up from the top of the base member, said needle park members located interior to the inner wall,
wherein the tray package is mounted in the tool nest.

5. The combination of claim 4, wherein the packaging machine additionally comprises:
an in-line printer associated therewith for printing package covers; and,
a punching apparatus for punching printed covers from a printed strip of cover material.

6. The combination of claim 5, wherein the packaging machine additionally comprises an apparatus for receiving a printed cover from the punching apparatus, and mounting the cover to the top of a tray package.

7. The combination of claim 5, wherein the tray package additionally comprises a cover for mounting to the top of the package.

8. A method of winding a double armed suture in a tray package, the method comprising:
I. providing a tray package having a top and a bottom, the tray package comprising:
a flat base member having a top and an outer periphery;
an outer wall extending up from the base member about the periphery of the base member;
an inner wall, interior to the outer wall, extending up from the top of the base member, said inner wall having a top and said inner wall spaced away from the outer wall to form a suture channel;
a plurality of door members extending from the top of the inner wall over the winding channel each such door member having a proximal end and a distal end, and opposed sides;
a plurality of openings between at least some of the door members for receiving channel winding pin members; and, at least two needle park members extending up from the top of the base member, said needle park members located interior to the inner wall;

II. providing a packaging machine, the packaging machine comprising:

a machine frame having a top, a bottom, sides and an interior;

a disc member rotatably mounted to the top of the frame, said disc member having a periphery, top, a bottom and a side about the periphery of the disc member;

a plurality of tool nests, each tool nest rotatably mounted to the top of the disc member, said tool nests comprising:

a nest frame, having a top, a bottom and sides; and, at least two winding pin members extending up from the top of the nest frame;

a rotatable tool mounted to the machine frame, said tool being displaceable downwardly to engage with the pin members on the nest frame, such that rotation of the tool will rotate the tool nest, wherein said rotatable tool has a top and a bottom;

a plurality of channel winding pin members extending down from the bottom of said rotatable tool;

a cam track member extending down from the bottom of the rotatable tool, said cam track member having a pair of opposed longitudinal sides and a pair of opposed curved ends connecting the longitudinal sides, said cam track member having a first width along the longitudinal sides and a second width along the curved ends, wherein the first width is greater than the second width; and, a stylus member movably mounted to the machine frame, for cooperation with the tool nests, comprising:

a stylus frame having a top, sides and a bottom;

a stylus mounted to the bottom of the stylus frame having a front nose member and a rear heel member separated by a suture opening, said stylus having a top surface; and, a door closing member extending down from the bottom of the stylus frame adjacent to the stylus, wherein the stylus member operatively engages the cam track member;

III. placing the tray package onto a nest member;

IV. providing a double-armed surgical suture comprising a suture having opposed ends, and having a surgical needle mounted to each end;

V. mounting the surgical needles in the needle parks; and

V. indexing the disc to a winding station where the rotatable tool is located, engaging the nest with the rotatable tool such that the channel winding pin members are displaced downwardly into the channel of the package, inserting the stylus into the suture channel, and rotating the tool nest and package to wind the suture in the suture channel.

9. The method of claim 8, wherein the packaging machine additionally comprises:

an in-line printer associated therewith for printing package covers; and, a punching apparatus for punching printed covers from a printed strip of cover material.

10. The method of claim 9, wherein the packaging machine additionally comprises an apparatus for receiving a printed cover from the punching apparatus, and mounting the cover to the top of a tray package.

11. The method of claim 10 additionally comprising the steps of:

feeding a flat strip of material to the in-line printer, the flat strip having a top and a bottom;

printing information of the top of the flat strip;

punching a cover having printed information from the flat strip; and, mounting the flat strip to the top of the package such that the printed information on the top of the package is visible.

* * * * *